US007572601B2

(12) United States Patent
Zhang et al.

(10) Patent No.: US 7,572,601 B2
(45) Date of Patent: Aug. 11, 2009

(54) COMPOSITIONS AND METHODS FOR DETERMINING OOCYTE DEVELOPMENT POTENTIAL

(75) Inventors: Xingqi Zhang, Buffalo Grove, IL (US); Edmond Confino, Chicago, IL (US); Ralph R. Kazer, Oak Park, IL (US)

(73) Assignee: Northwestern University, Evanston, IL (US)

( * ) Notice: Subject to any disclaimer, the term of this patent is extended or adjusted under 35 U.S.C. 154(b) by 294 days.

(21) Appl. No.: 11/251,983

(22) Filed: Oct. 17, 2005

(65) Prior Publication Data

US 2006/0147900 A1    Jul. 6, 2006

Related U.S. Application Data

(60) Provisional application No. 60/619,429, filed on Oct. 15, 2004.

(51) Int. Cl.
*C12Q 1/02* (2006.01)
(52) U.S. Cl. ...................................................... 435/29
(58) Field of Classification Search ........................ None
See application file for complete search history.

(56) References Cited

U.S. PATENT DOCUMENTS 7,041,648 B2 * 5/2006 Mantovani ................... 514/12

OTHER PUBLICATIONS

Zhang et al, "Pentraxin-3 gene expression in cumulus cells may be a molecular marker for egg quality," (Fertility and Sterility), vol. 80, Supp. 3, Sep. 2003, p. 81, available online Oct. 1, 2003.*
Hsu and Hsueh, "Tissue-Specific Bcl-2 Protein Partners in Apoptosis: an Ovarian Paradigm," Physiol Rev 80:593-614 (2000).
Lee et al., "Cumulus Cells Apoptosis as an Indicator to Predict the Quality of Oocytes and the Outcome of IVF-ET," J Assist Reprod Genet, (2001) 18:490-8.
Host et al., "Apoptosis in human cumulus cells in relation to zona pellucida thickness variation, maturation stage, and cleavage of the corresponding oocyte after intracytoplasmic sperm injection," Fertil Steril, (2002) 77:511-5.
El-Hefnawy and Zeleznik, "Synergism Between FSH and Activin in the Regulation of Proliferating Cell Nuclear Antigen (PCNA) and Cyclin D2 Expression in Rat Granulosa Cells," Endocrinlogy 142:4357-62, (2001).
Pangas et al., "Localization of the Activin Signal Transduction Components in Normal Human Ovarian Follicles: Implications for Autocrine and Paracrine Signaling in the Ovary," J Clin Endocr Metabol 87:2644-57, (2002).
Chun et al., "Interleukin-1B Suppresses Apoptosis in Rat Ovarian Follicles by Increasing Nitric Oxide Production," Endocrinology. 136:3120-7, (1995).
Chen and Ioannou, "Ribosomal Proteins in Cell Proliferation & Apoptosis," Intl Rev Immun (1999) 18:429-48.
Gewurz et al., "Structure and function of the pentraxins," Current Opinion in Immunology. 7:54-64 (1995).
Varani et al., "Knockout of Pentraxin 3, a Downstream Target of Growth Differentiation Factor-9, Causes Female Subfertility," Molecular Endocrinology. 16:1154-67 (2002).
Breviario et al., "Interleukin-l-Inducible Genes in Endothelial Cells," J. Biol. Chem., (1992) 267:22190-22197.

* cited by examiner

*Primary Examiner*—Ralph Gitomer
*Assistant Examiner*—Amanda P Wood
(74) *Attorney, Agent, or Firm*—Casimir Jones, S.C.

(57) ABSTRACT

The present invention relates to the field of reproduction (e.g., human reproduction). In particular, the present invention provides markers (e.g., pentraxin 3 and Annexin A6), and methods of using the same to determine oocyte development potential. The present invention also provides compositions and methods for modifying oocyte development potential and assays (e.g., using markers of the present invention) for detecting gene expression associated with oocyte development potential. Such compositions and methods find use in diagnostic, research and therapeutic applications.

3 Claims, 3 Drawing Sheets

```
                           SEQUENCE LISTING

<160> NUMBER OF SEQ ID NOS: 2

<210> SEQ ID NO 1
<211> LENGTH: 20
<212> TYPE: DNA
<213> ORGANISM: Artificial Sequence
<220> FEATURE:
<223> OTHER INFORMATION: Synthetic

<400> SEQUENCE: 1
gtgggtggag aggagaacaa                                              20

<210> SEQ ID NO 2
<211> LENGTH: 20
<212> TYPE: DNA
<213> ORGANISM: Artificial Sequence
<220> FEATURE:
<223> OTHER INFORMATION: Synthetic

<400> SEQUENCE: 2
aatctgcagg attcctccct                                              20
```

COMPOSITIONS AND METHODS FOR DETERMINING OOCYTE DEVELOPMENT POTENTIAL

This application claims priority to provisional patent application Ser. No. 60/619,429, filed on Oct. 15, 2004, which is herein incorporated by reference in its entirety.

This invention was funded, in part, under NIH grant U54 HD041857. The government may have certain rights in the invention.

FIELD OF THE INVENTION

The present invention relates to the field of reproduction (e.g., human reproduction). In particular, the present invention provides markers (e.g., pentraxin 3), and methods of using the same to determine oocyte development potential. The present invention also provides compositions and methods for modifying oocyte development potential and assays (e.g., using markers of the present invention) for detecting gene expression associated with oocyte development potential. Such compositions and methods find use in diagnostic, research and therapeutic applications.

BACKGROUND OF THE INVENTION

For many, prolonged attempts to become pregnant end in failure, resulting in their seeking assistance from an infertility clinic. Infertility can result from a great variety of causes, including anatomical, developmental, infectious and toxicological factors. Poor oocyte quality is the cause of infertility in a significant number of the 1.6 million American couples unable to conceive a child.

Various methods for assisted reproduction technology (ART) have been developed and used to assist couples unable to become pregnant naturally. Examples of ART include in vitro fertilization-embryo transfer (IVF-ET), intracytoplasmic sperm injection (ICSI), testicular sperm extraction (TESE), round spermatid injection (ROSI) and-embryo freezing. While ART is an important and general method for the treatment of sterile patients, there remain problems to be overcome, such as the low chance of success of becoming pregnant using ART.

In the United States, 15% of women of childbearing age have received an infertility treatment. There were 86,822 ART cycles reported in 1999, resulting in the birth of 30,285 babies (Assisted Reproductive Technology Success Rates National Summary and Fertility Clinic Reports. Centers for Disease Control/SART, Bethesda, Md., 1999). Thus, unfortunately, 69% of IVF cycles do not result in pregnancy. The woman's age appears as an important factor affecting the chance of live birth and risk of miscarriage when her own oocytes are used (See, e.g., Krisher, J. Anim. Sci., 82 (E Suppl) E14-E23 (2004)). Currently, about 10% of all ART cycles (9066 cycles in 1999) use donor oocytes. With her own oocytes, a 29-year old woman has about a 40% chance of achieveing pregnancy during an ART cycle. This figure drops to 32% by 36 years of age and nearly 0% by 46 years of age. However, when donor oocytes are used the chance of achieving pregnancy during ART stays around 40% regardless of the age of the patient. Thus, oocytes from older women are less competent, exemplifying the importance of oocyte quality (e.g., oocyte development potential) and the ability to characterize and/or determine the same.

As an oocyte grows and matures, it acquires the ability to resume and complete meiosis, successfully undergo the fertilization process, and initiate and sustain embryonic development. The mammalian oocyte and its surrounding somatic cells are interdependent throughout the growth and development of the oocyte and ovarian follicle of a female subject. Growing oocytes derive most substrates for energy metabolism and biosynthesis from granulosa cells. Cumulus cells are a sub-group of granulosa cells that surround the oocyte in an antral follicle and, because of their close proximity to the oocyte, play an important role in regulating oocyte maturation.

Abnormal patterns of gene expression in cumulus cells may lead to abnormal development of the oocyte (e.g., the inability of the oocyte to become fertilized), or the inability of the oocyte post fertilization (e.g., fertilized oocyte or embryo) to implant into the uterine wall of a female subject. What is needed are compositions and methods for understanding the regulation of oocyte growth and maturation. Specifically, compositions and methods are needed to determine oocyte development potential. Such compositions and methods may be able to provide markers for identifying the developmental potential of the oocyte and may provide compositions, methods and treatments useful for assisting normal oocyte development. For example, the ability to determine oocyte development potential could be used in the ART setting to identify oocytes possessing the highest probability of being fertilized and/or implanting within the uterus of a female subject, thereby decreasing costs associated with and increasing the probability of success using ARTs.

SUMMARY OF THE INVENTION

The present invention relates to the field of reproduction (e.g., human reproduction). In particular, the present invention provides markers (e.g., pentraxin 3), and methods of using the same to determine oocyte development potential. The present invention also provides compositions and methods for modifying oocyte development potential and assays (e.g., using markers of the present invention) for detecting gene expression associated with oocyte development potential. Such compositions and methods find use in diagnostic, research and therapeutic applications.

In some embodiments, the present invention provides a method of characterizing oocyte development potential of an oocyte comprising providing cumulus cells harvested from an oocyte cumulus complex comprising the oocyte and measuring the expression level of one or more oocyte development potential markers in the cumulus cells. In some embodiments, transvaginal aspiration is used to collect the oocyte. In some embodiments, the oocyte development potential marker is pentraxin 3. The present invention provides a variety of oocyte development potential markers that can be used in the methods of the present invention. Thus, the present invention is not limited to the use of pentraxin 3 to characterize oocyte development potential as other genes have been identified herein (e.g., See Table 1) whose expression is significantly altered and correlate with the oocyte development potential. For example, in some embodiments, the expression level of pentraxin 3 and one or more other genes is used to determine oocyte development potential. In some embodiments, enhanced expression of pentraxin 3 correlates with an increased likelihood of an oocyte becoming fertilized. In some embodiments, enhanced expression of pentraxin 3 correlates with an increased likelihood of an oocyte becoming implanted within the uterine wall of a female subject. In some embodiments, oocyte development potential is used to characterize one or more oocytes used in an ART cycle. In some embodiments, the ART cycle comprises IVF. Multiple types of ARTs are benefited by the compositions and methods of the present invention including, but not limited to, in vitro fertilization-embryo transfer (IVF-ET), intracytoplasmic sperm injection (ICSI), testicular sperm extraction (TESE), round spermatid injection (ROSI) and-embryo freezing.

The present invention also provides a method of determining the likelihood of an oocyte to become fertilized comprising providing cumulus cells from an oocyte cumulus complex, measuring the level of expression of one or more oocyte development potential markers in the cumulus cells, and correlating the level of expression of one or more oocyte development potential markers with the likelihood of the oocyte becoming fertilized. In some embodiments, transvaginal aspiration is used to collect an oocyte cumulus complex comprising the oocyte. In some embodiments, the oocyte development potential marker is pentraxin 3. In some embodiments, enhanced expression of pentraxin 3 is correlated with an increased likelihood of the oocyte becoming fertilized. In some embodiments, enhanced expression of pentraxin 3 further correlates with an increased likelihood of the oocyte becoming implanted within the uterine wall of a female subject. In some embodiments, determining the likelihood of an oocyte to become fertilized is used to screen one or more oocytes used in an ART cycle. In some embodiments, an oocyte that does not have an increased likelihood of becoming fertilized is not used in an ART cycle.

The present invention also provides a method of determining the likelihood of an oocyte implanting within the uterus of a female subject comprising providing cumulus cells from an oocyte cumulus complex, measuring the level of expression of one or more oocyte development potential markers in the cumulus cells; and correlating the level of expression of one or more oocyte development potential markers with the likelihood of the oocyte implanting within the uterus of a female subject. In some embodiments, the oocyte development potential marker is pentraxin 3. In some embodiments, enhanced expression of pentraxin 3 is correlated with an increased likelihood of the oocyte implanting within the uterus of a female subject. In some embodiments, determining the likelihood of an oocyte implanting within the uterus of a female subject is used to screen one or more oocytes used in an ART cycle. In some embodiments, an oocyte that does not have an increased likelihood of implanting within the uterus of a female subject is not used in an ART cycle.

DEFINITIONS

Figure 1:
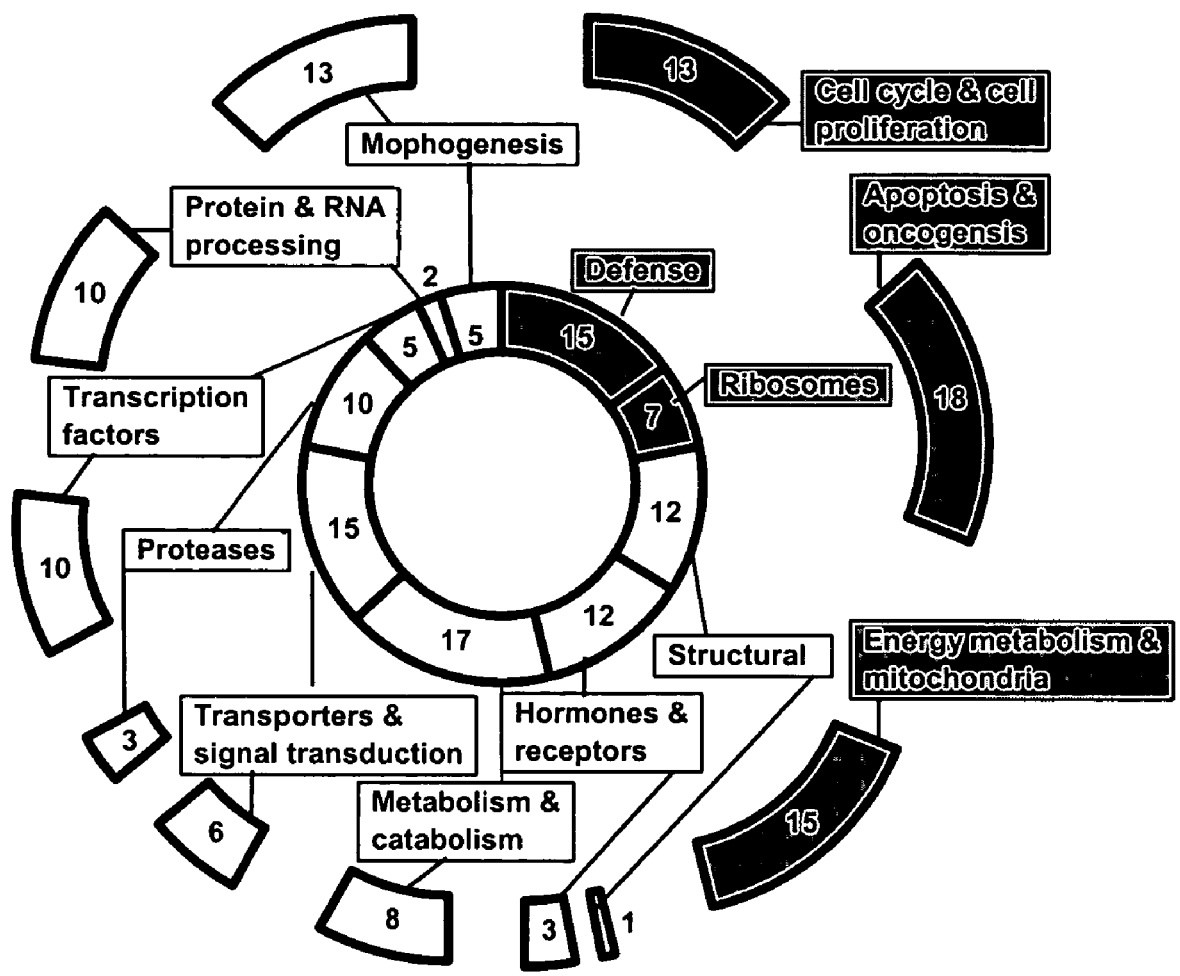
FIG. 1 shows a profile of gene expression in human cumulus cells. The outer ring represents functional groups of genes whose expression was altered >1.25-fold in cumulus cells from oocytes that developed into 8-cell embryos on day 3 (B) as compared to gene expression levels from oocytes that failed to fertilize (A) (p<0.01). The inner ring represents functional groups of genes whose expression was altered >1.25-fold in cumulus cells from Group A as compared to those in Group B. The shaded area represents genes whose expression was undetectable in the opposing group of cells.

The term "epitope" as used herein refers to that portion of an antigen that makes contact with a particular antibody.

When a protein or fragment of a protein is used to immunize a host animal, numerous regions of the protein may induce the production of antibodies that bind specifically to a given region or three-dimensional structure on the protein; these regions or structures are referred to as "antigenic determinants". An antigenic determinant may compete with the intact antigen (i.e., the "immunogen" used to elicit the immune response) for binding to an antibody.

The terms "specific binding" or "specifically binding" when used in reference to the interaction of an antibody and a protein or peptide means that the interaction is dependent upon the presence of a particular structure (i.e., the antigenic determinant or epitope) on the protein; in other words the antibody is recognizing and binding to a specific protein structure rather than to proteins in general. For example, if an antibody is specific for epitope "A," the presence of a protein containing epitope A (or free, unlabelled A) in a reaction containing labeled "A" and the antibody will reduce the amount of labeled A bound to the antibody.

As used herein, the terms "non-specific binding" and "background binding" when used in reference to the interaction of an antibody and a protein or peptide refer to an interaction that is not dependent on the presence of a particular structure (i.e., the antibody is binding to proteins in general rather than a particular structure such as an epitope).

As used herein, the term "subject" refers to any animal (e.g., a mammal), including, but not limited to, humans, non-human primates, rodents, and the like, which is to be the recipient of a particular treatment. Typically, the terms "subject" and "patient" are used interchangeably herein in reference to a human subject, unless indicated otherwise.

As used herein, the terms "subject into whom a fertilized egg is placed" and "subject into whom an embryo is placed" refers to a female subject that benefits from compositions and methods of the present invention (e.g., diagnostic markers and methods of using the same) into whom an in vitro fertilized egg (e.g., an embryo) is to be placed. A subject attempting to conceive may have one or more risk factors (e.g., previous problems with becoming pregnant (e.g., miscarriages, infertility for known or unknown reasons, etc)). A subject into whom a fertilized egg/embryo is placed generally refers to a subject that has attempted, unsuccessfully, to become pregnant in the past. However, the term also encompasses an individual who has not before attempted to become pregnant (e.g., through natural or artificial (e.g., in vitro fertilization) means)).

As used herein, the term "subject at risk for being unable to become pregnant" refers to a subject with one or more risk factors for being unable to become pregnant. Risk factors include, but are not limited to, age, genetic predisposition, environmental exposure, previous incidents of being unable to become pregnant (e.g., miscarriage, infertility for known or unknown reasons, etc.) and lifestyle.

As used herein, the terms "characterizing said oocyte" and "characterizing an oocyte" refer to the identification of one or more properties of an oocyte including, but not limited to, cumulus cell gene expression (e.g., pentraxin-3 and other genes provided in Table 1) associated with oocyte development potential (e.g., the ability of the oocyte to mature and develop (e.g., to implant within the uterine wall of a female subject)).

As used herein, the terms "oocyte development potential" and "developmental potential of the oocyte" refer generally to the maturation and developmental ability of an oocyte. This ability includes, but is not limited to, the ability of the oocyte to become fertilized (e.g., to become a fertilized oocyte or embryo), the ability of the fertilized oocyt to implant into the uterine wall of a female subject (e.g., from whom the oocyte was derived), or the ability of the oocyte to initiate and sustain embryonic development. Oocyte development potential may be characterized by the identification of the expression of one or more oocyte development potential markers (e.g., from a cumulus cell sample) including, but not limited to, the oocyte development potential markers disclosed herein.

As used herein, the terms "oocyte development potential marker," "oocyte development marker" and "development marker gene" refer to a gene whose expression level, or other characteristic, alone or in combination with other genes, is correlated with oocyte development potential (e.g., the ability of an oocyte to become fertilized, or, of a fertilized oocyte/embryo to become implanted within the uterine wall of a female subject). The correlation may relate to either an increased or decreased expression of the gene. For example, the expression (e.g., as compared to controls) of the gene may be indicative of the probability of an oocyte to implant into the uterine wall, and may be correlated with a prognosis in a subject attempting to become pregnant. Oocyte development marker expression status may be characterized using any suitable method, including but not limited to, those described in illustrative Examples 1-3 below, or described elsewhere herein.

As used herein, the term "oocyte cumulus complex" refers to the association of an oocyte with cumulus cells. The association of an oocyte with cumulus cells generally occurs within the follicle of a female subject. However, association of an oocyte with cumulus cells may also occur in vitro. For example, using assisted reproductive technologies (ARTs) described herein, it is common for one or more oocyte cumulus complexes to be harvested (e.g., aspirated) from ovarian follicles from a subject (e.g., a subject undergoing standard in vitro fertilization treatment including gonadotropin administration to induce multiple follicular development followed by transvaginal oocyte aspiration). Cumulus cells can be harvested (e.g., removed) from the oocyte cumuls complexes (e.g., in order to characterize gene expression profiles using compositions and methods provided by the present invention).

As used herein, the term "ART cycle" refers to a process in which an ART procedure is carried out, a woman has undergone ovarian stimulation or monitoring with the intent of having an ART procedure, or embryos have been obtained (e.g., frozen embryos thawed with the intent of transferring them to a woman). A cycle is considered to begin when a woman begins taking fertility drugs or having her ovaries monitored for follicle production.

As used herein, the term "a reagent that specifically detects expression levels" refers to reagents used to detect the expression of one or more genes (e.g., including, but not limited to, the development markers of the present invention). Examples of suitable reagents include, but are not limited to, nucleic acid probes capable of specifically hybridizing to the gene of interest, PCR primers capable of specifically amplifying the gene of interest, and antibodies capable of specifically binding to proteins expressed by the gene of interest. Other non-limiting examples can be found in the description and examples below.

As used herein, the term "detecting a decreased or increased expression relative to controls" refers to measuring the level of expression of a gene (e.g., the level of mRNA or protein) relative to the level in a control sample (e.g., a control sample representing oocytes likely to implant, or a control sample representing oocytes not likely to implant). Gene expression can be measured using any suitable method, including but not limited to, those described herein. Thus, as used herein, the term "enhanced expression of pentraxin 3" refers to an increased expression of pentraxin 3 relative to the level in a control sample (e.g., a control sample representing oocytes not likely to become fertilized or to implant).

As used herein, the term "detecting a change in gene expression in said sample in the presence of said test compound relative to the absence of said test compound" refers to measuring an altered level of expression (e.g., increased or decreased) of a gene (e.g., of pentraxin-3) in the presence of a test compound relative to the absence of the test compound. Gene expression can be measured using any suitable method, including but not limited to, those described in Examples 1-3 below.

As used herein, the term "instructions for using said kit for detecting oocyte development potential" includes instructions for using the reagents contained in the kit for the detection and characterization of oocyte development potential in a sample (e.g., cumulus cell sample) from a subject. In some embodiments, the instructions further comprise the statement of intended use required by the U.S. Food and Drug Administration (FDA) in labeling in vitro diagnostic products.

As used herein, the term "oocyte development potential expression profile map" refers to a presentation of expression levels of genes in a particular type of oocyte (e.g., an oocyte likely to implant in the uterus of a subject). The map may be presented as a graphical representation (e.g., on paper or on a computer screen), a physical representation (e.g., a gel or array) or a digital representation stored in computer memory. In preferred embodiments, maps are generated from pooled samples comprising samples from a plurality of oocytes correlated with the likelihood to implant or those correlated with not being likely to implant.

As used herein, the terms "computer memory" and "computer memory device" refer to any storage media readable by a computer processor. Examples of computer memory include, but are not limited to, RAM, ROM, computer chips, digital video disc (DVDs), compact discs (CDs), hard disk drives (HDD), and magnetic tape.

As used herein, the term "computer readable medium" refers to any device or system for storing and providing information (e.g., data and instructions) to a computer processor. Examples of computer readable media include, but are not limited to, DVDs, CDs, hard disk drives, magnetic tape and servers for streaming media over networks.

As used herein, the terms "processor" and "central processing unit" or "CPU" are used interchangeably and refer to a device that is able to read a program from a computer memory (e.g., ROM or other computer memory) and perform a set of steps according to the program.

As used herein, the term "providing a prognosis" refers to providing information regarding the likelihood of an oocyte to develop and/or mature (e.g., to implant into the uterine wall of a female subject) as determined, for example, by the diagnostic methods of the present invention).

As used herein, the term "non-human animals" refers to all non-human animals including, but not limited to, vertebrates such as rodents, non-human primates, ovines, bovines, ruminants, lagomorphs, porcines, caprines, equines, canines, felines, aves, etc.

As used herein, the term "gene transfer system" refers to any means of delivering a composition comprising a nucleic acid sequence to a cell or tissue. For example, gene transfer systems include, but are not limited to, vectors (e.g., retroviral, adenoviral, adeno-associated viral, and other nucleic acid-based delivery systems), microinjection of naked nucleic acid, polymer-based delivery systems (e.g., liposome-based and metallic particle-based systems), biolistic injection, and the like. As used herein, the term "viral gene transfer system" refers to gene transfer systems comprising viral elements (e.g., intact viruses, modified viruses and viral components such as nucleic acids or proteins) to facilitate delivery of the sample to a desired cell or tissue. As used herein, the term "adenovirus gene transfer system" refers to gene transfer systems comprising intact or altered viruses belonging to the family Adenoviridae.

As used herein, the term "site-specific recombination target sequences" refers to nucleic acid sequences that provide recognition sequences for recombination factors and the location where recombination takes place.

As used herein, the term "nucleic acid molecule" refers to any nucleic acid containing molecule, including but not limited to, DNA or RNA. The term encompasses sequences that include any of the known base analogs of DNA and RNA including, but not limited to, 4-acetylcytosine, 8-hydroxy-N6-methyladenosine, aziridinylcytosine, pseudoisocytosine, 5-(carboxyhydroxylmethyl) uracil, 5-fluorouracil, 5-bromouracil, 5-carboxymethylaminomethyl-2-thiouracil, 5-carboxymethylaminomethyluracil, dihydrouracil, inosine, N6-isopentenyladenine, 1-methyladenine, 1-methylpseudouracil, 1-methylguanine, 1-methylinosine, 2,2-dimethylguanine, 2-methyladenine, 2-methylguanine, 3-methylcytosine, 5-methylcytosine, N6-methyladenine, 7-methylguanine, 5-methylaminomethyluracil, 5-methoxyaminomethyl-2-thiouracil, beta-D-mannosylqueosine, 5'-methoxycarbonylmethyluracil, 5-methoxyuracil, 2-methylthio-N6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid, pseudouracil, queosine, 2-thiocytosine, and 2,6-diaminopurine.

The term "gene" refers to a nucleic acid (e.g., DNA) sequence that comprises coding sequences necessary for the production of a polypeptide, precursor, or RNA (e.g., rRNA, tRNA). The polypeptide can be encoded by a full length coding sequence or by any portion of the coding sequence so long as the desired activity or functional properties (e.g., enzymatic activity, ligand binding, signal transduction, immunogenicity, etc.) of the full-length or fragment are retained. The term also encompasses the coding region of a structural gene and the sequences located adjacent to the coding region on both the 5' and 3' ends for a distance of about 1 kb or more on either end such that the gene corresponds to the length of the full-length mRNA. Sequences located 5' of the coding region and present on the mRNA are referred to as 5' non-translated sequences. Sequences located 3' or downstream of the coding region and present on the mRNA are referred to as 3' non-translated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene that are transcribed into nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

As used herein, the term "heterologous gene" refers to a gene that is not in its natural environment. For example, a heterologous gene includes a gene from one species introduced into another species. A heterologous gene also includes a gene native to an organism that has been altered in some way (e.g., mutated, added in multiple copies, linked to non-native regulatory sequences, etc). Heterologous genes are distinguished from endogenous genes in that the heterologous gene sequences are typically joined to DNA sequences that are not found naturally associated with the gene sequences in the chromosome or are associated with portions of the chromosome not found in nature (e.g., genes expressed in loci where the gene is not normally expressed).

As used herein, the term "gene expression" refers to the process of converting genetic information encoded in a gene into RNA (e.g, mRNA, rRNA, tRNA, or snRNA) through "transcription" of the gene (i.e., via the enzymatic action of an RNA polymerase), and for protein encoding genes, into protein through "translation" of mRNA. Gene expression can be regulated at many stages in the process. "Up-regulation," "activation," or "enhanced expression" refers to regulation that increases the production of gene expression products (i.e., RNA or protein), while "down-regulation" or "repression" refers to regulation that decrease production. Molecules (e.g., transcription factors) that are involved in up-regulation or down-regulation are often called "activators" and "repressors," respectively.

In addition to containing introns, genomic forms of a gene may also include sequences located on both the 5' and 3' end of the sequences that are present on the RNA transcript. These sequences are referred to as "flanking" sequences or regions (these flanking sequences are located 5' or 3' to the non-translated sequences present on the mRNA transcript). The 5' flanking region may contain regulatory sequences such as promoters and enhancers that control or influence the transcription of the gene. The 3' flanking region may contain sequences that direct the termination of transcription, post-transcriptional cleavage and polyadenylation.

The term "wild-type" refers to a gene or gene product isolated from a naturally occurring source. A wild-type gene is that which is most frequently observed in a population and is thus arbitrarily designed the "normal" or "wild-type" form of the gene. In contrast, the term "modified" or "mutant" refers to a gene or gene product that displays modifications in sequence and or functional properties (i.e., altered characteristics, e.g., hypomethylation) when compared to the wild-type gene or gene product. It is noted that naturally occurring mutants can be isolated; these are identified by the fact that they have altered characteristics (including altered nucleic acid sequences) when compared to the wild-type gene or gene product.

DNA molecules are said to have "5' ends" and "3' ends" because mononucleotides are reacted to make oligonucleotides or polynucleotides in a manner such that the 5' phosphate of one mononucleotide pentose ring is attached to the 3' oxygen of its neighbor in one direction via a phosphodiester linkage. Therefore, an end of an oligonucleotides or polynucleotide, referred to as the "5' end" if its 5' phosphate is not linked to the 3' oxygen of a mononucleotide pentose ring and as the "3' end" if its 3' oxygen is not linked to a 5' phosphate of a subsequent mononucleotide pentose ring. The promoter and enhancer elements that direct transcription of a linked gene are generally located 5' or upstream of the coding region. However, enhancer elements can exert their effect even when located 3' of the promoter element and the coding region. Transcription termination and polyadenylation signals are located 3' or downstream of the coding region.

As used herein, the term "regulatory element" refers to a genetic element that controls some aspect of the expression of nucleic acid sequences. For example, a promoter is a regulatory element that facilitates the initiation of transcription of an operably linked coding region. Other regulatory elements include splicing signals, polyadenylation signals, termination signals, etc.

As used herein, the terms "nucleic acid molecule encoding," "DNA sequence encoding," and "DNA encoding" refer to the order or sequence of deoxyribonucleotides along a strand of deoxyribonucleic acid. The order of these deoxyribonucleotides determines the order of amino acids along the polypeptide (protein) chain. The DNA sequence thus codes for the amino acid sequence.

As used herein, the terms "an oligonucleotide having a nucleotide sequence encoding a gene" and "polynucleotide having a nucleotide sequence encoding a gene," means a nucleic acid sequence comprising the coding region of a gene or in other words the nucleic acid sequence that encodes a gene product. The coding region may be present in a cDNA, genomic DNA or RNA form. When present in a DNA form, the oligonucleotide or polynucleotide may be single-stranded (i.e., the sense strand) or double-stranded. Suitable control elements such as enhancers/promoters, splice junctions, polyadenylation signals, etc. may be placed in close proximity to the coding region of the gene if needed to permit proper initiation of transcription and/or correct processing of the primary RNA transcript. Alternatively, the coding region utilized in the expression vectors of the present invention may contain endogenous enhancers/promoters, splice junctions, intervening sequences, polyadenylation signals, etc. or a combination of both endogenous and exogenous control elements.

As used herein, the term "oligonucleotide," refers to a short length of single-stranded polynucleotide chain. Oligonucleotides are typically less than 200 residues long (e.g., between 15 and 100), however, as used herein, the term is also intended to encompass longer polynucleotide chains. Oligonucleotides are often referred to by their length. For example a 24 residue oligonucleotide is referred to as a "24-mer". Oligonucleotides can form secondary and tertiary structures by self-hybridizing or by hybridizing to other polynucleotides. Such structures can include, but are not limited to, duplexes, hairpins, cruciforms, bends, and triplexes.

As used herein, the terms "complementary" or "complementarity" are used in reference to polynucleotides (i.e., a sequence of nucleotides) related by the base-pairing rules. For example, for the sequence "5'-A-G-T-3'," is complementary to the sequence "3'-T-C-A-5'." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods that depend upon binding between nucleic acids.

The term "homology" refers to a degree of complementarity. There may be partial homology or complete homology (i.e., identity). A partially complementary sequence is a nucleic acid molecule that at least partially inhibits a completely complementary nucleic acid molecule from hybridizing to a target nucleic acid is "substantially homologous." The inhibition of hybridization of the completely complementary sequence to the target sequence may be examined using a hybridization assay (Southern or Northern blot, solution hybridization and the like) under conditions of low stringency. A substantially homologous sequence or probe will compete for and inhibit the binding (i.e., the hybridization) of a completely homologous nucleic acid molecule to a target under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target that is substantially non-complementary (e.g., less than about 30% identity); in the absence of non-specific binding the probe will not hybridize to the second non-complementary target.

When used in reference to a double-stranded nucleic acid sequence such as a cDNA or genomic clone, the term "substantially homologous" refers to any probe that can hybridize to either or both strands of the double-stranded nucleic acid sequence under conditions of low stringency as described above.

A gene may produce multiple RNA species that are generated by differential splicing of the primary RNA transcript. cDNAs that are splice variants of the same gene will contain regions of sequence identity or complete homology (representing the presence of the same exon or portion of the same exon on both cDNAs) and regions of complete non-identity (for example, representing the presence of exon "A" on cDNA 1 wherein cDNA 2 contains exon "B" instead). Because the two cDNAs contain regions of sequence identity they will both hybridize to a probe derived from the entire gene or portions of the gene containing sequences found on both cDNAs; the two splice variants are therefore substantially homologous to such a probe and to each other.

When used in reference to a single-stranded nucleic acid sequence, the term "substantially homologous" refers to any probe that can hybridize (i.e., it is the complement of) the single-stranded nucleic acid sequence under conditions of low stringency as described above.

As used herein, the term "hybridization" is used in reference to the pairing of complementary nucleic acids. Hybridization and the strength of hybridization (i.e., the strength of the association between the nucleic acids) is impacted by such factors as the degree of complementary between the nucleic acids, stringency of the conditions involved, the $T_m$ of the formed hybrid, and the G:C ratio within the nucleic acids. A single molecule that contains pairing of complementary nucleic acids within its structure is said to be "self-hybridized."

As used herein, the term "$T_m$" is used in reference to the "melting temperature." The melting temperature is the temperature at which a population of double-stranded nucleic acid molecules becomes half dissociated into single strands. The equation for calculating the $T_m$ of nucleic acids is well known in the art. As indicated by standard references, a simple estimate of the $T_m$ value maybe calculated by the equation: $T_m=81.5+0.41(\% \text{ G+C})$, when a nucleic acid is in aqueous solution at 1 M NaCl (See e.g., Anderson and Young, Quantitative Filter Hybridization, in Nucleic Acid Hybridization (1985)). Other references include more sophisticated computations that take structural as well as sequence characteristics into account for the calculation of $T_m$.

As used herein the term "stringency" is used in reference to the conditions of temperature, ionic strength, and the presence of other compounds such as organic solvents, under which nucleic acid hybridizations are conducted. Under "low stringency conditions" a nucleic acid sequence of interest will hybridize to its exact complement, sequences with single base mismatches, closely related sequences (e.g., sequences with 90% or greater homology), and sequences having only partial homology (e.g., sequences with 50-90% homology). Under 'medium stringency conditions," a nucleic acid sequence of interest will hybridize only to its exact complement, sequences with single base mismatches, and closely relation sequences (e.g., 90% or greater homology). Under "high stringency conditions," a nucleic acid sequence of interest will hybridize only to its exact complement, and (depending on conditions such a temperature) sequences with single base mismatches. In other words, under conditions of high stringency the temperature can be raised so as to exclude hybridization to sequences with single base mismatches.

"High stringency conditions" when used in reference to nucleic acid hybridization comprise conditions equivalent to binding or hybridization at 42° C. in a solution consisting of 5×SSPE (43.8 g/l NaCl, 6.9 g/l $NaH_2PO_4$ $H_2O$ and 1.85 g/l EDTA, pH adjusted to 7.4 with NaOH), 0.5% SDS, 5× Denhardt's reagent and 100 µg/ml denatured salmon sperm DNA followed by washing in a solution comprising 0.1×SSPE, 1.0% SDS at 42° C. when a probe of about 500 nucleotides in length is employed.

"Medium stringency conditions" when used in reference to nucleic acid hybridization comprise conditions equivalent to binding or hybridization at 42° C. in a solution consisting of 5×SSPE (43.8 g/l NaCl, 6.9 g/l $NaH_2PO_4$ $H_2O$ and 1.85 g/l EDTA, pH adjusted to 7.4 with NaOH), 0.5% SDS, 5× Denhardt's reagent and 100 µg/ml denatured salmon sperm DNA followed by washing in a solution comprising 1.0×SSPE, 1.0% SDS at 42° C. when a probe of about 500 nucleotides in length is employed.

"Low stringency conditions" comprise conditions equivalent to binding or hybridization at 42° C. in a solution consisting of 5×SSPE (43.8 g/l NaCl, 6.9 g/l $NaH_2PO_4$ $H_2O$ and 1.85 g/l EDTA, pH adjusted to 7.4 with NaOH), 0.1% SDS, 5× Denhardt's reagent (50× Denhardt's contains per 500 ml: 5 g Ficoll (Type 400, Pharamcia), 5 g BSA (Fraction V; Sigma)) and 100 µg/ml denatured salmon sperm DNA followed by washing in a solution comprising 5×SSPE, 0.1% SDS at 42° C. when a probe of about 500 nucleotides in length is employed.

The art knows well that numerous equivalent conditions may be employed to comprise low stringency conditions; factors such as the length and nature (DNA, RNA, base composition) of the probe and nature of the target (DNA, RNA, base composition, present in solution or immobilized, etc.) and the concentration of the salts and other components (e.g. the presence or absence of formamide, dextran sulfate, polyethylene glycol) are considered and the hybridization solution may be varied to generate conditions of low stringency hybridization different from, but equivalent to, the above listed conditions. In addition, the art knows conditions that promote hybridization under conditions of high stringency (e.g., increasing the temperature of the hybridization and/or wash steps, the use of formamide in the hybridization solution, etc.) (see definition above for "stringency").

As used herein, the term "primer" refers to an oligonucleotide, whether occurring naturally as in a purified restriction digest or produced synthetically, that is capable of acting as a point of initiation of synthesis when placed under conditions in which synthesis of a primer extension product that is complementary to a nucleic acid strand is induced, (i.e., in the presence of nucleotides and an inducing agent such as DNA polymerase and at a suitable temperature and pH). The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer must be sufficiently long to prime the synthesis of extension products in the presence of the inducing agent. The exact lengths of the primers will depend on many factors, including temperature, source of primer and the use of the method.

As used herein, the term "probe" refers to an oligonucleotide (i.e., a sequence of nucleotides), whether occurring naturally as in a purified restriction digest or produced synthetically, recombinantly or by PCR amplification, that is capable of hybridizing to at least a portion of another oligonucleotide of interest. A probe may be single-stranded or double-stranded. Probes are useful in the detection, identification and isolation of particular gene sequences. It is contemplated that any probe used in the present invention will be labeled with any "reporter molecule," so that is detectable in any detection system, including, but not limited to enzyme (e.g., ELISA, as well as enzyme-based histochemical assays), fluorescent, radioactive, and luminescent systems. It is not intended that the present invention be limited to any particular detection system or label.

As used herein the term "portion" when in reference to a nucleotide sequence (as in "a portion of a given nucleotide sequence") refers to fragments of that sequence. The fragments may range in size from four nucleotides to the entire nucleotide sequence minus one nucleotide (10 nucleotides, 20, 30, 40, 50, 100, 200, etc.).

As used herein, the term "amplification reagents" refers to those reagents (deoxyribonucleotide triphosphates, buffer, etc.), needed for amplification except for primers, nucleic acid template and the amplification enzyme. Typically, amplification reagents along with other reaction components are placed and contained in a reaction vessel (test tube, microwell, etc.).

As used herein, the terms "restriction endonucleases" and "restriction enzymes" refer to bacterial enzymes, each of which cut double-stranded DNA at or near a specific nucleotide sequence.

The terms "in operable combination," "in operable order," and "operably linked" as used herein refer to the linkage of nucleic acid sequences in such a manner that a nucleic acid molecule capable of directing the transcription of a given gene and/or the synthesis of a desired protein molecule is produced. The term also refers to the linkage of amino acid sequences in such a manner so that a functional protein is produced.

The term "isolated" when used in relation to a nucleic acid, as in "an isolated oligonucleotide" or "isolated polynucleotide" refers to a nucleic acid sequence that is identified and separated from at least one component or contaminant with which it is ordinarily associated in its natural source. Isolated nucleic acid is such present in a form or setting that is different from that in which it is found in nature. In contrast, non-isolated nucleic acids as nucleic acids such as DNA and RNA found in the state they exist in nature. For example, a given DNA sequence (e.g., a gene) is found on the host cell chromosome in proximity to neighboring genes; RNA sequences, such as a specific mRNA sequence encoding a specific protein, are found in the cell as a mixture with numerous other mRNAs that encode a multitude of proteins. However, isolated nucleic acid encoding a given protein includes, by way of example, such nucleic acid in cells ordinarily expressing the given protein where the nucleic acid is in a chromosomal location different from that of natural cells, or is otherwise flanked by a different nucleic acid sequence than that found in nature. The isolated nucleic acid, oligonucleotide, or polynucleotide may be present in single-stranded or double-stranded form. When an isolated nucleic acid, oligonucleotide or polynucleotide is to be utilized to express a protein, the oligonucleotide or polynucleotide will contain at a minimum the sense or coding strand (i.e., the oligonucleotide or polynucleotide may be single-stranded), but may contain both the sense and anti-sense strands (i.e., the oligonucleotide or polynucleotide may be double-stranded).

As used herein, the term "purified" or "to purify" refers to the removal of components (e.g., contaminants) from a sample. For example, antibodies are purified by removal of contaminating non-immunoglobulin proteins; they are also purified by the removal of immunoglobulin that does not bind to the target molecule. The removal of non-immunoglobulin proteins and/or the removal of immunoglobulins that do not bind to the target molecule results in an increase in the percent of target-reactive immunoglobulins in the sample. In another example, recombinant polypeptides are expressed in bacterial host cells and the polypeptides are purified by the removal of host cell proteins; the percent of recombinant polypeptides is thereby increased in the sample.

"Amino acid sequence" and terms such as "polypeptide" or "protein" are not meant to limit the amino acid sequence to the complete, native amino acid sequence associated with the recited protein molecule.

The term "native protein" as used herein to indicate that a protein does not contain amino acid residues encoded by vector sequences; that is, the native protein contains only those amino acids found in the protein as it occurs in nature. A native protein may be produced by recombinant means or may be isolated from a naturally occurring source.

As used herein the term "portion" when in reference to a protein (as in "a portion of a given protein") refers to fragments of that protein. The fragments may range in size from four amino acid residues to the entire amino acid sequence minus one amino acid.

The term "transgene" as used herein refers to a foreign gene that is placed into an organism by, for example, introducing the foreign gene into newly fertilized eggs or early embryos. The term "foreign gene" refers to any nucleic acid (e.g., gene sequence) that is introduced into the genome of an animal by experimental manipulations and may include gene sequences found in that animal so long as the introduced gene does not reside in the same location as does the naturally occurring gene.

As used herein, the term "vector" is used in reference to nucleic acid molecules that transfer DNA segment(s) from one cell to another. The term "vehicle" is sometimes used interchangeably with "vector." Vectors are often derived from plasmids, bacteriophages, or plant or animal viruses.

The term "expression vector" as used herein refers to a recombinant DNA molecule containing a desired coding sequence and appropriate nucleic acid sequences necessary for the expression of the operably linked coding sequence in a particular host organism. Nucleic acid sequences necessary for expression in prokaryotes usually include a promoter, an operator (optional), and a ribosome binding site, often along with other sequences. Eukaryotic cells are known to utilize promoters, enhancers, and termination and polyadenylation signals.

The terms "overexpression" and "overexpressing" and grammatical equivalents, are used in reference to levels of mRNA to indicate a level of expression approximately 3-fold higher (or greater) than that observed in a given tissue in a control or non-transgenic animal. Levels of mRNA are measured using any of a number of techniques known to those skilled in the art including, but not limited to Northern blot analysis. Appropriate controls are included on the Northern blot to control for differences in the amount of RNA loaded from each tissue analyzed (e.g., the amount of 28S rRNA, an abundant RNA transcript present at essentially the same amount in all tissues, present in each sample can be used as a means of normalizing or standardizing the mRNA-specific signal observed on Northern blots). The amount of mRNA present in the band corresponding in size to the correctly spliced transgene RNA is quantified; other minor species of RNA which hybridize to the transgene probe are not considered in the quantification of the expression of the transgenic mRNA.

The term "transfection" as used herein refers to the introduction of foreign DNA into eukaryotic cells. Transfection may be accomplished by a variety of means known to the art including calcium phosphate-DNA co-precipitation, DEAE-dextran-mediated transfection, polybrene-mediated transfection, electroporation, microinjection, liposome fusion, lipofection, protoplast fusion, retroviral infection, and biolistics.

The term "stable transfection" or "stably transfected" refers to the introduction and integration of foreign DNA into the genome of the transfected cell. The term "stable transfectant" refers to a cell that has stably integrated foreign DNA into the genomic DNA.

The term "transient transfection" or "transiently transfected" refers to the introduction of foreign DNA into a cell where the foreign DNA fails to integrate into the genome of the transfected cell. The foreign DNA persists in the nucleus of the transfected cell for several days. During this time the foreign DNA is subject to the regulatory controls that govern the expression of endogenous genes in the chromosomes. The term "transient transfectant" refers to cells that have taken up foreign DNA but have failed to integrate this DNA.

As used herein, the term "selectable marker" refers to the use of a gene that encodes an enzymatic activity that confers the ability to grow in medium lacking what would otherwise be an essential nutrient (e.g. the HIS3 gene in yeast cells); in addition, a selectable marker may confer resistance to an antibiotic or drug upon the cell in which the selectable marker is expressed. Selectable markers may be "dominant"; a dominant selectable marker encodes an enzymatic activity that can be detected in any eukaryotic cell line. Examples of dominant selectable markers include the bacterial aminoglycoside 3' phosphotransferase gene (also referred to as the neo gene) that confers resistance to the drug G418 in mammalian cells, the bacterial hygromycin G phosphotransferase (hyg) gene that confers resistance to the antibiotic hygromycin and the bacterial xanthine-guanine phosphoribosyl transferase gene (also referred to as the gpt gene) that confers the ability to grow in the presence of mycophenolic acid. Other selectable markers are not dominant in that their use must be in conjunction with a cell line that lacks the relevant enzyme activity. Examples of non-dominant selectable markers include the thymidine kinase (tk) gene that is used in conjunction with tk-cell lines, the CAD gene that is used in conjunction with CAD-deficient cells and the mammalian hypoxanthine-guanine phosphoribosyl transferase (hprt) gene that is used in conjunction with hprt-cell lines. A review of the use of selectable markers in mammalian cell lines is provided in Sambrook, J. et al., Molecular Cloning: A Laboratory Manual, 2nd ed., Cold Spring Harbor Laboratory Press, New York (1989) pp. 16.9-16.15.

As used herein, the term "cell culture" refers to any in vitro culture of cells. Included within this term are continuous cell lines (e.g., with an immortal phenotype), primary cell cultures, transformed cell lines, finite cell lines (e.g., non-transformed cells), and any other cell population maintained in vitro (e.g., oocytes and oocyte associated cells such as cumulus cells).

As used, the term "eukaryote" refers to organisms distinguishable from "prokaryotes." It is intended that the term encompass all organisms with cells that exhibit the usual characteristics of eukaryotes, such as the presence of a true nucleus bounded by a nuclear membrane, within which lie the chromosomes, the presence of membrane-bound organelles, and other characteristics commonly observed in eukaryotic organisms. Thus, the term includes, but is not limited to such organisms as fungi, protozoa, and animals (e.g., humans).

As used herein, the term "in vitro" refers to an artificial environment and to processes or reactions that occur within an artificial environment. In vitro environments can consist of, but are not limited to, test tubes and cell culture. The term "in vivo" refers to the natural environment (e.g., an animal or a cell) and to processes or reaction that occur within a natural environment.

The terms "test compound" and "candidate compound" refer to any chemical entity, pharmaceutical, drug, and the like that is a candidate for use to treat or prevent a disease, illness, sickness, or disorder of cellular or bodily function (e.g., inability of an oocyte to be fertilized or to implant into a uterine wall). Test compounds comprise both known and potential therapeutic compounds. A test compound can be determined to be therapeutic by screening using the screening methods of the present invention. In some embodiments of the present invention, test compounds include small molecules and antisense compounds.

As used herein, the term "sample" is used in its broadest sense. In one sense, it is meant to include a specimen or culture obtained from any source, as well as biological and environmental samples. Biological samples may be obtained from animals (including humans) and refers to a biological material or compositions found therein, including, but not limited to, bone marrow, blood, serum, platelet, plasma, interstitial fluid, urine, cerebrospinal fluid, nucleic acid, DNA, tissue, and purified or filtered forms thereof. Environmental samples include environmental material such as surface matter, soil, water, crystals and industrial samples. Such examples are not however to be construed as limiting the sample types applicable to the present invention.

As used herein, the term "immunoglobulin" or "antibody" refer to proteins that bind a specific antigen. Immunoglobulins include, but are not limited to, polyclonal, monoclonal, chimeric, and humanized antibodies, Fab fragments, F(ab')$_2$ fragments, and includes immunoglobulins of the following classes: IgG, IgA, IgM, IgD, IbE, and secreted immunoglobulins (sIg). Immunoglobulins generally comprise two identical heavy chains and two light chains. However, the terms "antibody" and "immunoglobulin" also encompass single chain antibodies and two chain antibodies.

As used herein, the term "antigen binding protein" refers to proteins that bind to a specific antigen. "Antigen binding proteins" include, but are not limited to, immunoglobulins, including polyclonal, monoclonal, chimeric, and humanized antibodies; Fab fragments, F(ab')$_2$ fragments, and Fab expression libraries; and single chain antibodies.

The term "epitope" as used herein refers to that portion of an antigen that makes contact with a particular immunoglobulin.

When a protein or fragment of a protein is used to immunize a host animal, numerous regions of the protein may induce the production of antibodies which bind specifically to a given region or three-dimensional structure on the protein; these regions or structures are referred to as "antigenic determinants". An antigenic determinant may compete with the intact antigen (i.e., the "immunogen" used to elicit the immune response) for binding to an antibody.

The terms "specific binding" or "specifically binding" when used in reference to the interaction of an antibody and a protein or peptide means that the interaction is dependent upon the presence of a particular structure (i.e., the antigenic determinant or epitope) on the protein; in other words the antibody is recognizing and binding to a specific protein structure rather than to proteins in general. For example, if an antibody is specific for epitope "A," the presence of a protein containing epitope A (or free, unlabelled A) in a reaction containing labeled "A" and the antibody will reduce the amount of labeled A bound to the antibody.

As used herein, the terms "non-specific binding" and "background binding" when used in reference to the interaction of an antibody and a protein or peptide refer to an interaction that is not dependent on the presence of a particular structure (i.e., the antibody is binding to proteins in general rather that a particular structure such as an epitope).

DETAILED DESCRIPTION OF THE INVENTION

The mammalian oocyte and its surrounding somatic cells are interdependent throughout the growth and development of the oocyte and ovarian follicle. Oocytes from primordial follicles fail to grow in vitro in the absence of granulosa cells (See, e.g., Eppig, J Exp Zool 209:345-53, (1979)). Growing oocytes derive most substrates for energy metabolism and biosynthesis from granulosa cells (See, e.g., Heller and Schultz, J Exp Zool. 214:355-64, (1980); Brower and Schultz, Dev Biol 90:144-53, (1982)). Cumulus cells are a sub-group of granulosa cells that surround the oocyte in an antral follicle and because of their close proximity to the oocyte play an important role in regulating oocyte maturation (See, e.g., Dekel and Beers, Dev Biol 75:247-54, (1980); Larsen et al., Dev Biol 113:517-21, (1986)).

The oocyte is also an important modulator of granulosa/cumulus cell function. In the mouse, cumulus expansion around the time of ovulation will not occur in the absence of the oocyte (See, e.g., Buccione et al., Developmental Biology. 138:16-25, (1990); Salustri et al., Developmental Biology. 138:26-32, (1990)). Recent studies demonstrate that growth and differentiation factor 9 (GDF-9) mediates this oocyte effect on cumulus expansion (See, e.g., Elvin et al., Molecular Endocrinology. 13:1035-48, (1999)). In addition, GDF-9, as well as bone morphorgenic protein-15 from oocytes, mediates other regulatory effects of the oocyte on granulosa/cumulus cells (See, e.g., Yan et al., Molecular Endocrinology. 15:854-66, (2001)). For example, GDF-9 inhibits FSH-induced steroidogenesis and LH receptor expression, and upregulates prostaglandin-endoperoxide synthase-2 (COX-2) and the type-2 receptor for prostaglandins in cumulus cells of preovulatory mouse follicles (See, e.g., Elvin et al., Molecular Endocrinology. 13:1035-48, (1999); Varani et al., Molecular Endocrinology. 16:1154-67, (2002)).

During development, a large variety of genes are turned on and off. The regulation of gene expression is highly controlled. Aberrant gene expression can lead to cancer or cell death. Monitoring the developmental status of a sample is made possible through the identification of genes expressed during normal development, and often disease states and/or abnormal development provide great insight into the genes expressed or not expressed during development. Furthermore, the ability to alter gene expression (e.g., enhancing or suppressing expression) plays a central role in research and therapeutic applications aimed at correcting abnormal development.

Cumulus cells of oocytes retrieved from infertile patients undergoing in vitro fertilization (IVF) treatments were studied in order to characterize gene expression profiles (e.g., in human cumulus cells) associated with oocyte development potential. The present invention provides the identification of 160 genetic markers (e.g., pentraxin 3 (Ptx3)) that display altered expression levels that are correlated with oocytes with greater or lesser oocyte development potential. Thus, the present invention provides use of these markers to characterize oocyte development.

Accordingly, the present invention provides markers (e.g., pentraxin 3 and Annexin A6), and methods of using the same to determine oocyte development potential. The present invention also provides compositions and methods for modifying oocyte development potential and assays (e.g., using markers of the present invention) for detecting gene expression associated with oocyte development potential. Such compositions and methods find use in diagnostic, research and therapeutic applications.

Accordingly, in some embodiments, the present invention provides a method of determining oocyte development potential comprising determining gene expression levels of markers of the present invention (e.g., Ptx3) in cumulus cells and associating the expression with the likelihood of the oocyte to become fertilized (e.g., to generate a fertilized oocyte or embryo). Additionally, the present invention provides a method of determining oocyte development potential comprising determining gene expression levels of markers of the present invention (e.g., Ptx3) in cumulus cells and associating the expression with the likelihood of the oocyte to implant in the uterine wall of a female subject (e.g., after fertilztion). Furthermore, compositions and methods of the present invention are contemplated to be useful with other methods (e.g., analysis of embryo cleavage rate and/or morphology) in order to determine oocyte development potential (e.g., the implantation potential of a fertilized oocyte).

When the genes detected using compositions and methods of the present invention are broken down into distinct groups by biological process, a substantial overlap in expression of genes involved in many biological processes was identified. However, genes implicated in certain biological processes were identified as being differentially regulated between the two groups of cumulus cells. Group A (oocytes that failed to fertilize) over-expressed immunological and ribosomal proteins indicative of shock and defense relative to Group B (oocytes that fertilized and developed into 8-cell embryos with little to no fragmentation on day 3 after oocyte retrieval). Genes involved in activities indicative of cell maintenance such as cell cycle, cell proliferation, apoptosis, oncogenesis, energy metabolism, and mitochondrial activities were over-expressed in Group B relative to Group A. The present invention provides assays for determining the gene expression profile and corresponding developmental status of cumulus cells and the enclosed oocyte, and correlating this profile to the probability of successful fertilization and/or implantation of a fertilized oocyte (e.g., an embryo produced through in vitro fertilization) into the uterus.

Compared to Group B, cumulus cells in Group A were from more heterogeneous follicles because the failure of an oocyte to fertilize in vitro is due to multiple factors, including sperm quality as well as the health status and the maturity of the follicle where the oocyte is originated. The possibility of follicular immaturity was significantly reduced, though not completely eliminated, by excluding cumulus cells from oocytes that did not complete meiotic maturation within the first 16 hours after oocyte retrieval.

Certain patterns of gene expression are readily apparent in the cumulus cells (See, e.g., Table 1). Genes that were involved in the regulation of apoptosis were increased in cumulus cells in Group B. Ovulation marks the transition of cumulus/granulosa cells to become luteal cells. Factors that promote and suppress apoptosis are both highly expressed in granulosa cells around the time of ovulation, indicating that the cells have the tendency to undergo apoptosis at the time of ovulation but this tendency is kept in check by anti-apoptotic factors such as members of the BCL-2 gene family (See, e.g., Hsu and Hsueh, Physiol Rev 80:593-614, (2000)). Previous studies have found that an increased population of cumulus cells undergoing apoptosis is associated with poor developmental outcome of the oocytes (See, e.g., Lee et al., J Assist Reprod Genet 18:490-8, (2001); Host et al., Fertil Steril 77:511-5, (2002)). The present invention demonstrates that BCL-2 family gene expression was enhanced in Group B cells.

Genes implicated in cell cycle/proliferation regulation were highly expressed in Group B cells. There was a 1.7-fold increase in PCNA gene expression in Group B over Group A. The expression of PCNA in human granulosa cells is known to be under the regulation of FSH and local paracrine factors such as inhibin/activin (See, e.g., El-Hefnawy and Zeleznik, Endocrinlogy 142:4357-62, (2001)).

Among the paracrine factors that are known to be involved in regulating follicular development, both Inhibin Beta-a and Beta-b subunit mRNAs were elevated in Group A. These two subunits comprise activin, which is expressed in granulosa cells of atretic follicles (See, e.g., Pangas et al., J Clin Endocr Metabol 87:2644-57, (2002)). Interleukin-1 is involved in apoptotic response in rat granulosa cells (See, e.g., Chun et al., Endocrinology. 136:3120-7, (1995)), and had an increased expression in cumulus cells in Group A. Three ribosomal proteins were upregulated in Group A. One of the proteins, L13a, is known to be involved in the induction of apoptosis in certain cell types (See, e.g., Chen and Ioannou, Intl Rev Immun 18:429-48, (1999)). In general, the present invention demonstrates increased apoptotic activities in cumulus complexes from oocytes that did not fertilize.

Pentraxin-3 was originally studied for its possible role in inflammatory reaction processes (See, e.g., Gewurz et al., Current Opinion in Immunology. 7:54-64, (1995)). It is one of the genes expressed in mouse granulosa cells that were regulated by oocyte GDF-9. Inactivation of this gene by targeted mutagenesis reduced the ability of oocytes to fertilize, potentially due to the disruption of the structural integrity of the cumulus complex (See, e.g., Varani et al., Molecular Endocrinology. 16:1154-67, (2002)).

The present invention demonstrates that pentraxin-3 is expressed in human cumulus cells. Furthermore, an increase in pentraxin-3 gene expression is demonstrated in cumulus cells from oocytes that developed into 8-cells on day 3. There was as much as a 12-fold increase in pentraxin-3 expression in cumulus cells from oocytes that became 8-cells on day 3 and, at least some of them, initiated implantation following transfer. This may be an under-estimation because embryos that were transferred but did not implant were also included in this group. Nonetheless, the present invention demonstrates that the differential expression of pentraxin-3 is a more discriminative index for implantation than the number of cells present in the embryo.

The present invention demonstrates that most of the differentially expressed genes associated with oocyte development potential had a change of 1-2 fold, less than the 4-12 fold increase in pentraxin-3 expression as revealed by real time PCR. However, it has been noted that microarrays may underestimate the magnitude change, compared with more quantitative techniques such as Northern blot analysis and real-time PCR (See, e.g., Chuaqui et al., Nature Genet 32 (Suppl): 509-14, (2002)).

As the efficacy of assisted reproductive technologies (ART) improves, the incidence of high-order multiple gestations has increased significantly (See, e.g., Wright et al., Morbidity & Mortality Weekly Report. Surveillance Summaries/CDC. 52(9):1-16, (2003)). Negative impact of multifetal gestation on the infants and mothers is well documented (See, e.g., Pharoah and Cooke, Archives of Disease in Childhood Fetal & Neonatal Edition. 75:F174-7, (1996); Blickstein and Keith, Current Opinion in Obstetrics & Gynecology. 15(2):113-7, (2003); Conde-Agudelo et al., Obstetrics & Gynecology. 95(6 Pt 1):899-904, (2000)). The present invention provides markers that can predict oocyte development potential (e.g., the ability of an oocyte to become fertilized or to implant into the uterus) and eliminates the need to replace multiple embryos without compromising pregnancy rates after ART treatment, thereby reducing the incidence of high-order multiple gestations.

Oocyte Development Markers

Identification of Markers

The present invention provides markers whose expression is specifically altered in cumulus cells associated with oocytes possessing development potential (e.g., the ability to become fertilized or to implant into the uterine wall of a female subject). Specifically, experiments conducted during the development of the present invention resulted in the identification oocyte development markers (e.g., pentraxin 3) whose expression level was altered (e.g., increased) in oocytes possessing a greater likelihood of becoming fertilized and/or implanting into the uterus once fertilized (See Examples 1-3). Such markers find use in the characterization of oocytes (e.g., for use in in vitro fertilization).

In some embodiments, the present invention provides a method for detection of expression of oocyte development markers (e.g., pentraxin 3). In preferred embodiments, expression is measured directly (e.g., at the RNA or protein level). In some embodiments, expression is detected in tissue samples (e.g., aspirated tissue). In other embodiments, expression is detected in bodily fluids (e.g., including but not limited to, plasma, serum, whole blood, mucus, and urine).

The present invention further provides panels and kits for the detection of markers. In preferred embodiments, the presence of an oocyte development marker (e.g., pentraxin 3) is used to characterize the likelihood of an oocyte to become fertilized or to implant into the uterus once fertilized. For example, the detection of elevated levels of pentraxin 3, as compared to controls, in a sample is indicative of an oocyte that is likely to become fertilized and/or that will undergo normal implantation into the uterus. Such information is contemplated to be extremely useful in lowering risks associated with ART technologies (e.g., multiple gestations). In addition, if a subject is found to not be responsive to drugs (e.g., gonadotropin) used to induce multiple follicular development, the expense and inconvenience of such therapies can be avoided.

The present invention is not limited to the markers described above. Any suitable marker that correlates with oocyte development potential may be utilized, including but not limited to, those described in the illustrative examples below (e.g., pentraxin 3 or those listed in Table 1). Additional markers are also contemplated to be within the scope of the present invention. Any suitable method may be utilized to identify and characterize oocyte development markers suitable for use in the methods of the present invention, including but not limited to, those described in illustrative Examples 1-3 below. For example, in some embodiments, markers identified as being up or down-regulated in oocytes with development potential using the methods of the present invention can be further characterized using tissue microarray, immunohistochemistry, Northern blot analysis, siRNA or antisense RNA inhibition, mutation analysis, investigation of expression with clinical outcome, as well as other methods disclosed herein.

In some embodiments, the present invention provides a panel for the analysis of a plurality of markers (e.g., pentraxin 3, BCL 2 family members, PCNA, etc.). The panel allows for the simultaneous analysis of multiple markers correlating with oocyte development potential. For example, a panel may include markers identified as correlating with fertilization of an oocyte or implantation of a fertilized oocyte/embryo in a subject that is/are likely or not likely to respond to a given treatment (e.g., drug or pharmaceutical administered to increase fertility). Depending on the subject, panels may be analyzed alone or in combination in order to provide the best possible prognosis. Markers for inclusion on a panel are selected by screening for their predictive value using any suitable method, including but not limited to, those described in the illustrative examples below.

In other embodiments, the present invention provides an expression profile map comprising expression profiles of oocyte development potential of various populations of oocytes. Such maps can be used for comparison with patient samples. Any suitable method may be utilized, including but not limited to, by computer comparison of digitized data. The comparison data is used to provide prognoses (e.g., likelihood of becoming pregnant) to patients.

Detection of RNA

In some preferred embodiments, detection of oocyte development markers (e.g., including but not limited to, those disclosed herein) is detected by measuring the expression of corresponding mRNA in a tissue or other sample (e.g., cumulus cell sample). mRNA expression may be measured by any suitable method, including but not limited to, those disclosed below.

In some embodiments, RNA is detection by Northern blot analysis. Northern blot analysis involves the separation of RNA and hybridization of a complementary labeled probe.

In still further embodiments, RNA (or corresponding cDNA) is detected by hybridization to an oligonucleotide probe. A variety of hybridization assays using a variety of technologies for hybridization and detection are available. For example, in some embodiments, TaqMan assay (PE Biosystems, Foster City, Calif.; See e.g., U.S. Pat. Nos. 5,962,233 and 5,538,848, each of which is herein incorporated by reference) is utilized. The assay is performed during a PCR reaction. The TaqMan assay exploits the 5'-3' exonuclease activity of the AMPLITAQ GOLD DNA polymerase. A probe consisting of an oligonucleotide with a 5'-reporter dye (e.g., a fluorescent dye) and a 3'-quencher dye is included in the PCR reaction. During PCR, if the probe is bound to its target, the 5'-3' nucleolytic activity of the AMPLITAQ GOLD polymerase cleaves the probe between the reporter and the quencher dye. The separation of the reporter dye from the quencher dye results in an increase of fluorescence. The signal accumulates with each cycle of PCR and can be monitored with a fluorimeter.

In yet other embodiments, reverse-transcriptase PCR (RT-PCR) is used to detect the expression of RNA. In RT-PCR, RNA is enzymatically converted to complementary DNA or "cDNA" using a reverse transcriptase enzyme. The cDNA is then used as a template for a PCR reaction. PCR products can be detected by any suitable method, including but not limited to, gel electrophoresis and staining with a DNA specific stain or hybridization to a labeled probe. In some embodiments, the quantitative reverse transcriptase PCR with standardized mixtures of competitive templates method described in U.S.

Pat. Nos. 5,639,606, 5,643,765, and 5,876,978 (each of which is herein incorporated by reference) is utilized.

Detection of Protein

In other embodiments, gene expression of oocyte development markers is detected by measuring the expression of the corresponding protein or polypeptide. Protein expression may be detected by any suitable method. In some embodiments, proteins are detected by immunohistochemistry method. In other embodiments, proteins are detected by their binding to an antibody raised against the protein. The generation of antibodies is described below.

Antibody binding is detected by techniques known in the art (e.g., radioimmunoassay, ELISA (enzyme-linked immunosorbant assay), "sandwich" immunoassays, immunoradiometric assays, gel diffusion precipitation reactions, immunodiffusion assays, in situ immunoassays (e.g., using colloidal gold, enzyme or radioisotope labels, for example), Western blots, precipitation reactions, agglutination assays (e.g., gel agglutination assays, hemagglutination assays, etc.), complement fixation assays, immunofluorescence assays, protein A assays, and immunoelectrophoresis assays, etc).

In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many methods are known in the art for detecting binding in an immunoassay and are within the scope of the present invention.

In some embodiments, an automated detection assay is utilized. Methods for the automation of immunoassays include those described in U.S. Pat. Nos. 5,885,530, 4,981,785, 6,159,750, and 5,358,691, each of which is herein incorporated by reference. In some embodiments, the analysis and presentation of results is also automated. For example, in some embodiments, software that generates a prognosis based on the presence or absence of a series of proteins corresponding to oocyte development markers is utilized.

In other embodiments, the immunoassay is as described in U.S. Pat. Nos. 5,599,677 and 5,672,480; each of which is herein incorporated by reference.

In some embodiments, the present invention provides a pentraxin 3 antigen ELISA (e.g., comprising monoclonal anti-pentraxin 3 antibodies) to determine oocyte development potential. The present invention demonstrates that pentraxin 3 levels are significantly increased in oocytes likely to become fertilized and/or likely to implant into the uterus.

Data Analysis

In some embodiments, a computer-based analysis program is used to translate the raw data generated by the detection assay (e.g., the presence, absence, or amount of a given marker or markers) into data of predictive value for a clinician. The clinician can access the predictive data using any suitable means. Thus, in some preferred embodiments, the present invention provides the further benefit that the clinician, who is not likely to be trained in genetics or molecular biology, need not understand the raw data. The data is presented directly to the clinician in its most useful form. The clinician is then able to immediately utilize the information in order to optimize the care of the subject.

The present invention contemplates any method capable of receiving, processing, and transmitting the information to and from laboratories conducting the assays, information provides, medical personal, and subjects. For example, in some embodiments of the present invention, a sample (e.g., a biopsy or a serum or urine sample) is obtained from a subject and submitted to a profiling service (e.g., clinical lab at a medical facility, genomic profiling business, etc.), located in any part of the world (e.g., in a country different than the country where the subject resides or where the information is ultimately used) to generate raw data. Where the sample comprises a tissue or other biological sample, the subject may visit a medical center to have the sample obtained and sent to the profiling center, or subjects may collect the sample themselves (e.g., a urine sample) and directly send it to a profiling center. Where the sample comprises previously determined biological information, the information may be directly sent to the profiling service by the subject (e.g., an information card containing the information may be scanned by a computer and the data transmitted to a computer of the profiling center using an electronic communication systems). Once received by the profiling service, the sample is processed and a profile is produced (i.e., expression data), specific for the prognostic information desired for the subject.

The profile data is then prepared in a format suitable for interpretation by a treating clinician. For example, rather than providing raw expression data, the prepared format may represent a prognostic assessment (e.g., likelihood of an oocyte to implant in the uterus) for the subject, along with recommendations for particular options. The data may be displayed to the clinician by any suitable method. For example, in some embodiments, the profiling service generates a report that can be printed for the clinician (e.g., at the point of care) or displayed to the clinician on a computer monitor.

In some embodiments, the information is first analyzed at the point of care or at a regional facility. The raw data is then sent to a central processing facility for further analysis and/or to convert the raw data to information useful for a clinician or patient. The central processing facility provides the advantage of privacy (all data is stored in a central facility with uniform security protocols), speed, and uniformity of data analysis. The central processing facility can then control the fate of the data following treatment of the subject. For example, using an electronic communication system, the central facility can provide data to the clinician, the subject, or researchers.

In some embodiments, the subject is able to directly access the data using the electronic communication system. The subject may chose further intervention or counseling based on the results. In some embodiments, the data is used for research use. For example, the data may be used to further optimize the inclusion or elimination of markers as useful indicators of a particular condition.

Kits

In yet other embodiments, the present invention provides kits for the detection and characterization of oocyte development potential. In some embodiments, the kits contain antibodies (e.g., anti-pentraxin 3 antibodies or oligonucleotide probes) specific for an oocyte development potential marker (e.g., pentraxin 3), in addition to detection reagents and buffers. In other embodiments, the kits contain reagents specific for the detection of mRNA or cDNA (e.g., oligonucleotide probes or primers). In preferred embodiments, the kits contain all of the components necessary to perform a detection assay, including all controls, directions for performing assays, and any necessary software for analysis and presentation of results.

In vivo Imaging

In some embodiments, in vivo imaging techniques are used to visualize the expression of oocyte development markers in an animal (e.g., a human or non-human mammal). For example, in some embodiments, oocyte development potential marker mRNA or protein is labeled using a labeled antibody specific for the oocyte development potential marker. A specifically bound and labeled antibody can be detected in an individual using an in vivo imaging method, including, but not limited to, radionuclide imaging, positron emission tomography, computerized axial tomography, X-ray or magnetic resonance imaging method, fluorescence detection, and chemiluminescent detection. Methods for generating antibodies to the oocyte development markers of the present invention are described below.

The in vivo imaging methods of the present invention are useful in the diagnosis and characterization (e.g., response to treatment) of oocyte development potential that express the oocyte development markers of the present invention. In vivo imaging is used to visualize the presence of a marker indicative of the oocyte development potential. Such techniques allow for near instantaneous prognostic information (e.g., without the need to run a gel). The in vivo imaging methods of the present invention are also useful for providing prognoses to patients (e.g., a woman attempting to become pregnant). For example, the presence of a marker indicative of oocyte development potential (e.g., an oocyte likely to become fertilized or that will implant) can be detected. The in vivo imaging methods of the present invention can further be used to detect sites (e.g., follicles) from which to harvest oocytes.

In some embodiments, reagents (e.g., antibodies) specific for the oocyte development markers of the present invention are fluorescently labeled. The labeled antibodies can be introduced into a subject (e.g., orally or parenterally). Fluorescently labeled antibodies are detected using any suitable method (e.g., using the apparatus described in U.S. Pat. No. 6,198,107, herein incorporated by reference).

In other embodiments, antibodies are radioactively labeled. The use of antibodies for in vivo diagnosis is well known in the art. Sumerdon et al., (Nucl. Med. Biol 17:247-254 (1990)) have described an optimized antibody-chelator for the radioimmunoscintographic imaging of tumors using Indium-111 as the label. Griffin et al., (J Clin Onc 9:631-640 (1991)) have described the use of this agent in detecting tumors in patients suspected of having recurrent colorectal cancer. The use of similar agents with paramagnetic ions as labels for magnetic resonance imaging is known in the art (Lauffer, Magnetic Resonance in Medicine 22:339-342 (1991)). The label used will depend on the imaging modality chosen. Radioactive labels such as Indium-111, Technetium-99m, or Iodine-131 can be used for planar scans or single photon emission computed tomography (SPECT). Positron emitting labels such as Fluorine-19 can also be used for positron emission tomography (PET). For MRI, paramagnetic ions such as Gadolinium (III) or Manganese (II) can be used.

Radioactive metals with half-lives ranging from 1 hour to 3.5 days are available for conjugation to antibodies, such as scandium-47 (3.5 days) gallium-67 (2.8 days), gallium-68 (68 minutes), technetiium-99m (6 hours), and indium-111 (3.2 days), of which gallium-67, technetium-99m, and indium-111 are preferable for gamma camera imaging, gallium-68 is preferable for positron emission tomography.

A useful method of labeling antibodies with such radiometals is by means of a bifunctional chelating agent, such as diethylenetriaminepentaacetic acid (DTPA), as described, for example, by Khaw et al. (Science 209:295 (1980)) for In-111 and Tc-99m, and by Scheinberg et al. (Science 215:1511 (1982)). Other chelating agents may also be used, but the 1-(p-carboxymethoxybenzyl) EDTA and the carboxycarbonic anhydride of DTPA are advantageous because their use permits conjugation without affecting the antibody's immunoreactivity substantially.

Another method for coupling DPTA to proteins is by use of the cyclic anhydride of DTPA, as described by Hnatowich et al. (Int. J. Appl. Radiat. Isot. 33:327 (1982)) for labeling of albumin with In-111, but which can be adapted for labeling of antibodies. A suitable method of labeling antibodies with Tc-99m which does not use chelation with DPTA is the pretinning method of Crockford et al., (U.S. Pat. No. 4,323,546, herein incorporated by reference).

A preferred method of labeling immunoglobulins with Tc-99m is that described by Wong et al. (Int. J. Appl. Radiat. Isot., 29:251 (1978)) for plasma protein, and recently applied successfully by Wong et al. (J. Nucl. Med., 23:229 (1981)) for labeling antibodies.

In the case of the radiometals conjugated to the specific antibody, it is likewise desirable to introduce as high a proportion of the radiolabel as possible into the antibody molecule without destroying its immunospecificity. A further improvement may be achieved by effecting radiolabeling in the presence of the specific oocyte development potential marker of the present invention, to insure that the antigen binding site on the antibody will be protected. The antigen is separated after labeling.

In still further embodiments, in vivo biophotonic imaging (Xenogen, Alameda, Calif.) is utilized for in vivo imaging. This real-time in vivo imaging utilizes luciferase. The luciferase gene is incorporated into cells, microorganisms, and animals (e.g., as a fusion protein with a oocyte development potential marker of the present invention). When active, it leads to a reaction that emits light. A CCD camera and software is used to capture the image and analyze it.

Antibodies

The present invention provides isolated antibodies. In preferred embodiments, the present invention provides monoclonal antibodies that specifically bind to an isolated polypeptide comprised of at least five amino acid residues of an oocyte development potential marker described herein (e.g., pentraxin 3). These antibodies find use in the diagnostic methods described herein.

An antibody against an oocyte development potential protein of the present invention may be any monoclonal or polyclonal antibody, as long as it can recognize the protein. Antibodies can be produced by using a protein of the present invention as the antigen according to a conventional antibody or antiserum preparation process.

The present invention contemplates the use of both monoclonal and polyclonal antibodies. Any suitable method may be used to generate the antibodies used in the methods and compositions of the present invention, including but not limited to, those disclosed herein. For example, for preparation of a monoclonal antibody, protein, as such, or together with a suitable carrier or diluent is administered to an animal (e.g., a mammal) under conditions that permit the production of antibodies. For enhancing the antibody production capability, complete or incomplete Freund's adjuvant may be administered. Normally, the protein is administered once every 2 weeks to 6 weeks, in total, about 2 times to about 10 times. Animals suitable for use in such methods include, but are not limited to, primates, rabbits, dogs, guinea pigs, mice, rats, sheep, goats, etc.

For preparing monoclonal antibody-producing cells, an individual animal whose antibody titer has been confirmed (e.g., a rabbit or mouse) is selected, and 2 days to 5 days after the final immunization, its spleen or lymph node is harvested and antibody-producing cells contained therein are fused with myeloma cells to prepare the desired monoclonal antibody producer hybridoma. Measurement of the antibody titer in antiserum can be carried out, for example, by reacting the labeled protein, as described hereinafter and antiserum and then measuring the activity of the labeling agent bound to the antibody. The cell fusion can be carried out according to known methods, for example, the method described by Koehler and Milstein (Nature 256:495 (1975)).

Examples of myeloma cells include NS-1, P3U1, SP2/0, AP-1 and the like. The proportion of the number of antibody producer cells (spleen cells) and the number of myeloma cells to be used is preferably about 1:1 to about 20:1. PEG (preferably PEG 1000-PEG 6000) is preferably added in concentration of about 10% to about 80%. Cell fusion can be carried out efficiently by incubating a mixture of both cells at about 20° C. to about 40° C., preferably about 30° C. to about 37° C. for about 1 minute to 10 minutes.

Various methods may be used for screening for a hybridoma producing the antibody (e.g., against a oocyte development potential protein or autoantibody of the present invention). For example, where a supernatant of the hybridoma is added to a solid phase (e.g., microplate) to which antibody is adsorbed directly or together with a carrier and then an anti-immunoglobulin antibody (if mouse cells are used in cell fusion, anti-mouse immunoglobulin antibody is used) or Protein A labeled with a radioactive substance or an enzyme is added to detect the monoclonal antibody against the protein bound to the solid phase. Alternately, a supernatant of the hybridoma is added to a solid phase to which an anti-immunoglobulin antibody or Protein A is adsorbed and then the protein labeled with a radioactive substance or an enzyme is added to detect the monoclonal antibody against the protein bound to the solid phase.

Selection of the monoclonal antibody can be carried out according to any known method or its modification. Normally, a medium for animal cells to which HAT (hypoxanthine, aminopterin, thymidine) are added is employed. Any selection and growth medium can be employed as long as the hybridoma can grow. For example, RPMI 1640 medium containing 1% to 20%, preferably 10% to 20% fetal bovine serum, GIT medium containing 1% to 10% fetal bovine serum, a serum free medium for cultivation of a hybridoma (SFM-101, Nissui Seiyaku) and the like can be used. Normally, the cultivation is carried out at 20° C. to 40° C., preferably 37° C. for about 5 days to 3 weeks, preferably 1 week to 2 weeks under about 5% $CO_2$ gas. The antibody titer of the supernatant of a hybridoma culture can be measured according to the same manner as described above with respect to the antibody titer of the anti-protein in the antiserum.

Separation and purification of a monoclonal antibody (e.g., against an oocyte development potential marker of the present invention) can be carried out according to the same manner as those of conventional polyclonal antibodies such as separation and purification of immunoglobulins, for example, salting-out, alcoholic precipitation, isoelectric point precipitation, electrophoresis, adsorption and desorption with ion exchangers (e.g., DEAE), ultracentrifugation, gel filtration, or a specific purification method wherein only an antibody is collected with an active adsorbent such as an antigen-binding solid phase, Protein A or Protein G and dissociating the binding to obtain the antibody.

Polyclonal antibodies may be prepared by any known method or modifications of these methods including obtaining antibodies from patients. For example, a complex of an immunogen (an antigen against the protein) and a carrier protein is prepared and an animal is immunized by the complex according to the same manner as that described with respect to the above monoclonal antibody preparation. A material containing the antibody against is recovered from the immunized animal and the antibody is separated and purified.

As to the complex of the immunogen and the carrier protein to be used for immunization of an animal, any carrier protein and any mixing proportion of the carrier and a hapten can be employed as long as an antibody against the hapten, which is crosslinked on the carrier and used for immunization, is produced efficiently. For example, bovine serum albumin, bovine cycloglobulin, keyhole limpet hemocyanin, etc. may be coupled to an hapten in a weight ratio of about 0.1 part to about 20 parts, preferably, about 1 part to about 5 parts per 1 part of the hapten.

In addition, various condensing agents can be used for coupling of a hapten and a carrier. For example, glutaraldehyde, carbodiimide, maleimide activated ester, activated ester reagents containing thiol group or dithiopyridyl group, and the like find use with the present invention. The condensation product as such or together with a suitable carrier or diluent is administered to a site of an animal that permits the antibody production. For enhancing the antibody production capability, complete or incomplete Freund's adjuvant may be administered. Normally, the protein is administered once every 2 weeks to 6 weeks, in total, about 3 times to about 10 times.

The polyclonal antibody is recovered from blood, ascites and the like, of an animal immunized by the above method. The antibody titer in the antiserum can be measured according to the same manner as that described above with respect to the supernatant of the hybridoma culture. Separation and purification of the antibody can be carried out according to the same separation and purification method of immunoglobulin as that described with respect to the above monoclonal antibody.

The protein used herein as the immunogen is not limited to any particular type of immunogen. For example, an oocyte development potential marker of the present invention (further including a gene having a nucleotide sequence partly altered) can be used as the immunogen. Further, fragments of the protein may be used. Fragments may be obtained by any methods including, but not limited to expressing a fragment of the gene, enzymatic processing of the protein, chemical synthesis, and the like.

Drug Screening

In some embodiments, the present invention provides drug screening assays (e.g., to screen for fertility drugs). The screening methods of the present invention utilize oocyte development markers identified using the methods of the present invention (e.g., including but not limited to, pentraxin 3). For example, in some embodiments, the present invention provides methods of screening for compound that alter (e.g., increase or decrease) the expression of oocyte development potential marker genes. In some embodiments, candidate compounds are small molecules or pharmaceuticals that enhance expression of oocyte development markers (e.g., pentraxin 3).

In one screening method, candidate compounds are evaluated for their ability to alter oocyte development potential marker expression by contacting a compound with a cell (e.g., granulosa (e.g., cumulus) cell)) expressing a oocyte development potential marker and then assaying for the effect of the candidate compounds on expression. In some embodiments, the effect of candidate compounds on expression of an oocyte development potential marker gene is assayed for by detecting the level of oocyte development potential marker mRNA expressed by the cell. mRNA expression can be detected by any suitable method. In other embodiments, the effect of candidate compounds on expression of oocyte development potential marker genes is assayed by measuring the level of polypeptide encoded by the oocyte development markers. The level of polypeptide expressed can be measured using any suitable method, including but not limited to, those disclosed herein.

Specifically, the present invention provides screening methods for identifying modulators, i.e., candidate or test compounds or agents (e.g., proteins, peptides, peptidomimetics, peptoids, small molecules or other drugs) that bind to oocyte development markers (e.g., pentraxin 3) of the present invention, have an stimulatory (or inhibitory) effect on, for example, oocyte development potential marker expression or oocyte development markers activity, or have a stimulatory or inhibitory effect on, for example, the expression or activity of an oocyte development potential marker substrate. Compounds thus identified can be used to modulate the activity of target gene products (e.g., oocyte development potential marker genes) either directly or indirectly in a therapeutic protocol, to elaborate the biological function of the target gene product, or to identify compounds that disrupt normal target gene interactions. Compounds that inhibit the activity or expression of oocyte development markers are useful in the treatment of infertility.

In one embodiment, the invention provides assays for screening candidate or test compounds that are substrates of an oocyte development potential marker protein or polypeptide or a biologically active portion thereof. In another embodiment, the invention provides assays for screening candidate or test compounds that bind to or modulate the activity of an oocyte development potential marker protein or polypeptide or a biologically active portion thereof.

The test compounds of the present invention can be obtained using any of the numerous approaches in combinatorial library methods known in the art, including biological libraries; peptoid libraries (libraries of molecules having the functionalities of peptides, but with a novel, non-peptide backbone, which are resistant to enzymatic degradation but which nevertheless remain bioactive; see, e.g., Zuckennann et al., J. Med. Chem. 37: 2678-85 (1994)); spatially addressable parallel solid phase or solution phase libraries; synthetic library methods requiring deconvolution; the 'one-bead one-compound' library method; and synthetic library methods using affinity chromatography selection. The biological library and peptoid library approaches are preferred for use with peptide libraries, while the other four approaches are applicable to peptide, non-peptide oligomer or small molecule libraries of compounds (See, e.g., Lam, Anticancer Drug Des. 12:145 (1997)).

Examples of methods for the synthesis of molecular libraries can be found in the art, for example in: DeWitt et al., Proc. Natl. Acad. Sci. U.S.A. 90:6909 (1993); Erb et al., Proc. Nad. Acad. Sci. USA 91:11422 (1994); Zuckermann et al., J. Med. Chem. 37:2678 (1994); Cho et al., Science 261:1303 (1993); Carrell et al., Angew. Chem. Int. Ed. Engl. 33.2059 (1994); Carell et al., Angew. Chem. Int. Ed. Engl. 33:2061 (1994); and Gallop et al., J. Med. Chem. 37:1233 (1994).

Libraries of compounds may be presented in solution (e.g., Houghten, Biotechniques 13:412-421 (1992)), or on beads (Lam, Nature 354:82-84 (1991)), chips (Fodor, Nature 364: 555-556 (1993)), bacteria or spores (U.S. Pat. No. 5,223,409; herein incorporated by reference), plasmids (Cull et al., Proc. Nad. Acad. Sci. USA 89:18651869 (1992)) or on phage (Scott and Smith, Science 249:386-390 (1990); Devlin Science 249: 404-406 (1990); Cwirla et al., Proc. Natl. Acad. Sci. 87:6378-6382 (1990); Felici, J. Mol. Biol. 222:301 (1991)).

In one embodiment, an assay is a cell-based assay in which a cell that expresses an oocyte development potential marker protein or biologically active portion thereof is contacted with a test compound, and the ability of the test compound to modulate the oocyte development potential marker's activity is determined. Determining the ability of the test compound to modulate oocyte development potential marker activity can be accomplished by monitoring, for example, B cell stimulation or changes in enzymatic activity. The cell, for example, can be of mammalian origin.

The ability of the test compound to modulate oocyte development potential marker binding to a compound, e.g., an oocyte development potential marker substrate, can also be evaluated. This can be accomplished, for example, by coupling the compound, e.g., the substrate, with a radioisotope or enzymatic label such that binding of the compound, e.g., the substrate, to an oocyte development potential marker can be determined by detecting the labeled compound, e.g., substrate, in a complex.

Alternatively, the oocyte development potential marker is coupled with a radioisotope or enzymatic label to monitor the ability of a test compound to modulate oocyte development potential marker binding to an oocyte development marker substrate in a complex. For example, compounds (e.g., substrates) can be labeled with $^{125}I$, $^{35}S$ $^{14}C$ or $^{3}H$, either directly or indirectly, and the radioisotope detected by direct counting of radioemmission or by scintillation counting. Alternatively, compounds can be enzymatically labeled with, for example, horseradish peroxidase, alkaline phosphatase, or luciferase, and the enzymatic label detected by determination of conversion of an appropriate substrate to product.

The ability of a compound (e.g., an oocyte development potential marker substrate) to interact with an oocyte development potential marker with or without the labeling of any of the interactants can be evaluated. For example, a microphysiometer can be used to detect the interaction of a compound with an oocyte development potential marker without the labeling of either the compound or the oocyte development potential marker (McConnell et al. Science 257:1906-1912 (1992)). As used herein, a "microphysiometer" (e.g., Cytosensor) is an analytical instrument that measures the rate at which a cell acidifies its environment using a light-addressable potentiometric sensor (LAPS). Changes in this acidification rate can be used as an indicator of the interaction between a compound and oocyte development markers.

In yet another embodiment, a cell-free assay is provided in which an oocyte development potential marker protein or biologically active portion thereof is contacted with a test compound and the ability of the test compound to bind to the oocyte development potential marker protein or biologically active portion thereof is evaluated. Preferred biologically active portions of the oocyte development markers proteins to be used in assays of the present invention include fragments that participate in interactions with substrates or other proteins, e.g., fragments with high surface probability scores.

Cell-free assays involve preparing a reaction mixture of the oocyte development potential target gene protein and the test compound under conditions and for a time sufficient to allow the two components to interact and bind, thus forming a complex that can be removed and/or detected.

The interaction between two molecules can also be detected, e.g., using fluorescence energy transfer (FRET) (See, e.g., Lakowicz et al., U.S. Pat. No. 5,631,169; Stavrianopoulos et al., U.S. Pat. No. 4,968,103; each of which is herein incorporated by reference). A fluorophore label is selected such that a first donor molecule's emitted fluorescent energy will be absorbed by a fluorescent label on a second, 'acceptor' molecule, which in turn is able to fluoresce due to the absorbed energy.

Alternately, the 'donor' protein molecule may simply utilize the natural fluorescent energy of tryptophan residues. Labels are chosen that emit different wavelengths of light, such that the 'acceptor' molecule label may be differentiated from that of the 'donor'. Since the efficiency of energy transfer between the labels is related to the distance separating the molecules, the spatial relationship between the molecules can be assessed. In a situation in which binding occurs between the molecules, the fluorescent emission of the 'acceptor' molecule label in 1 5 the assay should be maximal. An FRET binding event can be conveniently measured through standard fluorometric detection means well known in the art (e.g., using a fluorimeter).

In another embodiment, determining the ability of the oocyte development potential marker proteins to bind to a target molecule can be accomplished using real-time Biomolecular Interaction Analysis (BIA) (See, e.g., Sjolander and Urbaniczky, Anal. Chem. 63:2338-2345 (1991) and Szabo et al. Curr. Opin. Struct. Biol. 5:699-705 (1995)). "Surface plasmon resonance" or "BIA" detects biospecific interactions in real time, without labeling any of the interactants (e.g., BIAcore). Changes in the mass at the binding surface (indicative of a binding event) result in alterations of the refractive index of light near the surface (the optical phenomenon of surface plasmon resonance (SPR)), resulting in a detectable signal that can be used as an indication of real-time reactions between biological molecules.

In one embodiment, the target gene product or the test substance is anchored onto a solid phase. The target gene product/test compound complexes anchored on the solid phase can be detected at the end of the reaction. Preferably, the target gene product can be anchored onto a solid surface, and the test compound, (which is not anchored), can be labeled, either directly or indirectly, with detectable labels discussed herein.

It may be desirable to immobilize oocyte development markers, an oocyte development marker antibody or its target molecule to facilitate separation of complexed from non-complexed forms of one or both of the proteins, as well as to accommodate automation of the assay. Binding of a test compound to an oocyte development potential marker protein, or interaction of an oocyte development potential marker protein with a target molecule in the presence and absence of a candidate compound, can be accomplished in any vessel suitable for containing the reactants. Examples of such vessels include microtiter plates, test tubes, and micro-centrifuge tubes. In one embodiment, a fusion protein can be provided that adds a domain that allows one or both of the proteins to be bound to a matrix. For example, glutathione-S-transferase-oocyte development potential marker fusion proteins or glutathione-S-transferase/target fusion proteins can be adsorbed onto glutathione Sepharose beads (Sigma Chemical, St. Louis, Mo.) or glutathione-derivatized microtiter plates, which are then combined with the test compound or the test compound and either the non-adsorbed target protein or oocyte development potential marker protein, and the mixture incubated under conditions conducive for complex formation (e.g., at physiological conditions for salt and pH). Following incubation, the beads or microtiter plate wells are washed to remove any unbound components, the matrix immobilized in the case of beads, complex determined either directly or indirectly, for example, as described above.

Alternatively, the complexes can be dissociated from the matrix, and the level of oocyte development markers binding or activity determined using standard techniques. Other techniques for immobilizing either oocyte development potential marker proteins or a target molecule on matrices include using conjugation of biotin and streptavidin. Biotinylated oocyte development potential marker protein or target molecules can be prepared from biotin-NHS (N-hydroxy-succinimide) using techniques known in the art (e.g., biotinylation kit, Pierce Chemicals, Rockford, EL), and immobilized in the wells of streptavidin-coated 96 well plates (Pierce Chemical).

In order to conduct the assay, the non-immobilized component is added to the coated surface containing the anchored component. After the reaction is complete, unreacted components are removed (e.g., by washing) under conditions such that any complexes formed will remain immobilized on the solid surface. The detection of complexes anchored on the solid surface can be accomplished in a number of ways. Where the previously non-immobilized component is pre-labeled, the detection of label immobilized on the surface indicates that complexes were formed. Where the previously non-immobilized component is not pre-labeled, an indirect label can be used to detect complexes anchored on the surface; e.g., using a labeled antibody specific for the immobilized component (the antibody, in turn, can be directly labeled or indirectly labeled with, e.g., a labeled anti-IgG antibody).

This assay is performed utilizing antibodies reactive with oocyte development potential marker protein or target molecules but which do not interfere with binding of the oocyte development potential marker proteins to its target molecule. Such antibodies can be derivatized to the wells of the plate, and unbound target or oocyte development potential marker proteins trapped in the wells by antibody conjugation. Methods for detecting such complexes, in addition to those described above for the GST-immobilized complexes, include immunodetection of complexes using antibodies reactive with the oocyte development potential marker protein or target molecule, as well as enzyme-linked assays which rely on detecting an enzymatic activity associated with the oocyte development potential marker protein or target molecule.

Alternatively, cell free assays can be conducted in a liquid phase. In such an assay, the reaction products are separated from unreacted components, by any of a number of standard techniques, including, but not limited to: differential centrifugation (See, e.g., Rivas and Minton, Trends Biochem Sci 18:284-7 (1993)); chromatography (gel filtration chromatography, ion-exchange chromatography); electrophoresis (See, e.g., Ausubel et al., eds. Current Protocols in Molecular Biology 1999, J. Wiley: New York.); and immunoprecipitation (See, e.g., for example, Ausubel et al., eds. Current Protocols in Molecular Biology 1999, J. Wiley: New York). Such resins and chromatographic techniques are known to one skilled in the art (See e.g., Heegaard J. Mol. Recognit 11:141-8 (1998); Hageand Tweed J. Chromatogr. Biomed. Sci. Appl 699:499-525 (1997)). Further, fluorescence energy transfer may also be conveniently utilized, as described herein, to detect binding without further purification of the complex from solution.

The assay can include contacting the oocyte development potential marker protein or biologically active portion thereof with a known compound that binds the oocyte development potential marker to form an assay mixture, contacting the assay mixture with a test compound, and determining the ability of the test compound to interact with an oocyte development potential marker protein, wherein determining the ability of the test compound to interact with an oocyte development potential marker protein includes determining the ability of the test compound to preferentially bind to oocyte development markers or biologically active portion thereof, or to modulate the activity of a target molecule, as compared to the known compound.

To the extent that oocyte development markers can, in vivo, interact with one or more cellular or extracellular macromolecules, such as proteins, inhibitors of such an interaction are useful. A homogeneous assay can be used can be used to identify inhibitors.

For example, a preformed complex of the target gene product and the interactive cellular or extracellular binding partner product is prepared such that either the target gene products or their binding partners are labeled, but the signal generated by the label is quenched due to complex formation (see, e.g., U.S. Pat. No. 4,109,496, herein incorporated by reference, that utilizes this approach for immunoassays). The addition of a test substance that competes with and displaces one of the species from the preformed complex will result in the generation of a signal above background. In this way, test substances that disrupt target gene product-binding partner interaction can be identified. Alternatively, oocyte development potential marker protein can be used as a "bait protein" in a two-hybrid assay or three-hybrid assay (see, e.g., U.S. Pat. No. 5,283,317; Zervos et al., Cell 72:223-232 (1993); Madura et al., J. Biol. Chem. 268.12046-12054 (1993); Bartel et al., Biotechniques 14:920-924 (1993); Iwabuchi et al., Oncogene 8:1693-1696 (1993); and Brent WO 94/10300; each of which is herein incorporated by reference), to identify other proteins, that bind to or interact with oocyte development potential marker ("oocyte development potential-binding proteins") and are involved in oocyte development potential marker activity. Such oocyte development potential markerbinding proteins can be activators or inhibitors of signals by the oocyte development potential marker proteins or targets as, for example, downstream elements of an oocyte development markers-mediated signaling pathway.

Modulators of oocyte development potential marker expression can also be identified. For example, a cell or cell free mixture is contacted with a candidate compound and the expression of oocyte development potential marker mRNA or protein evaluated relative to the level of expression of oocyte development potential marker mRNA or protein in the absence of the candidate compound. When expression of oocyte development potential marker mRNA or protein is greater in the presence of the candidate compound than in its absence, the candidate compound is identified as a stimulator of oocyte development potential marker mRNA or protein expression (e.g., GDF-9). Alternatively, when expression of oocyte development potential marker mRNA or protein is less (i.e., statistically significantly less) in the presence of the candidate compound than in its absence, the candidate compound is identified as an inhibitor of oocyte development potential marker mRNA or protein expression. The level of oocyte development potential marker mRNA or protein expression can be determined by methods described herein for detecting oocyte development markers mRNA or protein.

A modulating agent can be identified using a cell-based or a cell free assay, and the ability of the agent to modulate the activity of an oocyte development potential marker protein can be confirmed in vivo, (e.g., in an animal such as an animal model for infertility) or cumulus cells from a subject, or cells from an cumulus cell line.

This invention further pertains to novel agents identified by the above-described screening assays (e.g., agents that can be used in compositions (e.g., pharmaceuticals) used in infertility therapies). Accordingly, it is within the scope of this invention to further use an agent identified as described herein (e.g., an oocyte development potential marker modulating agent, or an enhancer of oocyte development potential marker expression) in an appropriate animal model (such as those described herein) to determine the efficacy, toxicity, side effects, or mechanism of action, of treatment with such an agent. Furthermore, novel agents identified by the above-described screening assays can be used for treatments, for example, as described herein.

EXPERIMENTAL

The following examples are provided in order to demonstrate and further illustrate certain preferred embodiments and aspects of the present invention and are not to be construed as limiting the scope thereof.

Example 1

Materials And Methods

Experiments conducted during the development of the present invention were approved by the Institutional Review Board at Northwestern University. Cumulus cells were collected for this study from patients who consented to participate. The patients went through standard IVF treatment that included gonadotropin administration to induce multiple follicular development and trans-vaginal oocyte aspiration. Details of the IVF treatment have been described (See, e.g., Chen et al.,. Fertility & Sterility. 80:75-9, (2003)).

Cumulus cells. After the oocyte-cumulus complexes were aspirated from ovarian follicles and identified under dissection microscope, cumulus cells were removed from the oocyte with 24-guage needles. The oocytes were cultured individually under appropriate culture conditions for fertilization in vitro (See, e.g., Chen et al.,. Fertility & Sterility. 80:75-9, (2003)). Fertilization and subsequent embryo development for each oocyte was recorded 16-18 hours and 64-66 hours after insemination, respectively. Cumulus cells from immature oocytes (e.g., absence of the first polar body in the oocyte or cumulus expansion) were not collected. Cumulus cells from oocytes that were fertilized by the means of intracytoplasmic sperm injection were also excluded.

The cumulus cells were processed to extract RNA either immediately (for quantification of Ptx3 expression) or after freezing and storage at −80° C. until the oocyte's in vitro development outcome was known. To isolate total RNA, cumulus cells were lysed in Trizol reagent (Invitrogen, Carlsbad, Calif.) and centrifuged in the presence of chloroform. Absence of significant DNA contamination or RNA degradation was verified by micro-electrophoresis on a Bioanalyzer 2100 (Agilent Technologies, Palo Alto, Calif.). RNA samples were processed for further analysis if the absorbance ratio at wavelengths of 260/280 nm was greater than 1.8 (indicative of little DNA contamination) and the ratio of 28s/18s ribosomal RNA greater than 2.0 (indicative of little RNA degradation).

Microarray analysis. Cumulus cells were pooled into two groups before RNA extraction: those from oocytes that failed to fertilize (Group A), and those from oocytes that fertilized and developed into 8-cell embryos with little or no fragmentation on day 3 after oocyte retrieval (Group B). Each patient cycle contributed cumulus cells to groups A and B, although not in the same number or proportion.

One to 1.5 μg of total RNA were used as templates to obtain double-stranded cDNA, using the MessageAMP kit (Ambion Inc., Austin, Tex.). The cDNA sample was applied to a filter cartridge provided in the MessageAMP kit to remove RNA, primers, salt, and enzymes. The sample was then used as a template in the in vitro transcription reaction to obtain labeled antisense RNA (aRNA) in the presence of Biotin-16-UTP (Roche Molecular Biochemicals, Nutley, N.J.) and Biotin-11-CTP (Perkin Elmer Life Science, Boston, Mass.). The quality and size of each biotin-labeled aRNA were verified using the Agilent Bioanalyzer 2100. Twenty micrograms of the biotin-labeled aRNA were fragmented for hybridization to U133A chips from Affymetrix (Santa Clara, Calif.), following Affymetrix protocols. Each U133A chip contains 45,000 probe sets representing more than 39,000 transcripts derived from approximately 33,000 well-substantiated human genes (Affymetrix).

Relevance of differential expression was assessed using replicate experiments and a t-test. The differences between the two cohorts of samples (A and B) were averaged and the standard deviation calculated between these differences. The P-value was calculated using a t-distribution. A P-value less than 0.01 and a fold difference of +/−1.25 were used as the cutoff to select differentially expressed genes. Functions of the differentially expressed genes were deduced by gene ontology annotations, using an online analysis at www.gene-ontology.org. A summary of cumulus cell gene expression (e.g., dependent on the in vitro development of their enclosd oocytes) in functional categories is outlined in FIG. 1 and Table 1 (below).

Polymerase chain reaction. To verify the presence of Ptx3 mRNA in human cumulus cells, total RNA from pooled cumulus cells was reverse transcribed into single-stranded cDNA using poly-dT primers (Invitrogen). The cDNA was amplified by 30 cycles of polymerase chain reaction (PCR) using primers specific for human Ptx3 (custom-made by Integrated DNA Technologies, Coralville, Iowa). The left and right primers consisted of nucleotide sequences of 5'-GTGGGTGGAGAGGAGAACAA-3' (SEQ ID NO: 1) and 5'-AATCTGCAGGATTCCTCCCT-3' (SEQ ID NO: 2), respectively, corresponding to nucleotides 861-880 and 1046-1027 of the human pentraxin 3 mRNA sequence (See, e.g., Breviario et al., J. Biol. Chem. 267:22190-22197, (1992); Genbank Accession NM 002852). The amplification product has an expected size of 186 base pairs.

A quantitative, real-time PCR method with a Taqman probe (See, e.g., Heid et al., Genome Research. 6:986-94 (1996)) was employed to determine the relative abundance of Ptx3 mRNA in cumulus cells. Total RNA from freshly collected, individual cumulus complexes was reverse transcribed (i.e. one cumulus complex per reverse transcription reaction) into single-stranded cDNA using random hexamers (Applied Biosystems, Foster City, Calif.). The cDNA from each cumulus complex was subjected to real-time PCR in triplicate reactions, using an Applied Biosystems' automated DNA Sequence Detection System (PRISM® 7900HT). The reagents for real-time PCR, including PCR primers and Taqman probe, were purchased from Applied Biosystems (Assay ID=Hs00173615m1).

The Taqman probe has a nucleotide sequence corresponding to the specific amplification product (e.g., Ptx3) and is labeled with a fluorescent dye, which is quenched by a fluorescent-inhibiting molecule present in the Taqman probe. When Taqman probe is associated with target sequence, the 5'-nuclease activity present in the real-time PCR reaction removes the fluorescent-labeled nucleotide from the Taqman probe, releasing it from the inhibition by the quencher molecule. The accumulation of free fluorescent dye in the reaction can be quantified and corresponds to the accumulation of the specific amplification product. The number of PCR cycles required for the accumulation of the amplification product to reach a fixed threshold is inversely correlated to the amount of target mRNA present in the sample.

Data was analyzed according to supplier's (e.g., Applied Biosystems) recommendations. After real time PCR amplifications were completed, the accumulation of amplification product was plotted against the number of amplification cycles. A threshold cycle number was selected in the linear region of the accumulation curve for the amplification product. The relative abundance of Ptx3 mRNA was the difference between the number of cycles of amplification for Ptx3 to reach the threshold and the number of cycles of amplification for 18s RNA to reach the threshold in the same sample. The use of 18s RNA as a reference has been demonstrated (See, e.g., Radonic et al., Biochemical & Biophysical Research Communications. 313:856-62, (2004)). Differences in the relative abundance of Ptx3 mRNA between cumulus samples were analyzed by a two-tailed t test.

Example 2

Gene Expression Profiling By Microarray Analysis

The first replicate analyzed cumulus cells from nine patients (one cycle for each patient), with 32 cumulus complexes in Group A and 23 in Group B. The cause of infertility was tubal disease for two patients, endometriosis for one and unexplained for the rest of the nine patients. In the second replicate, cumulus cells were collected from 11 patients (one cycle per patient), with 43 cumulus complexes in Group A and 25 in Group B. The cause of infertility was tubal disease for one, endometriosis for two patients, polycystic ovarian syndrome for two, and unexplained for the other six patients. Some of the embryos corresponding to Group B were transferred in the same cycle and others (surplus after transfer) were cryopreserved for future use. Twelve clinical pregnancies (e.g., via observation of fetal heart beats) resulted from the 20 IVF cycles, similar to the overall pregnancy rates in the IVF center during the development of the present invention.

Most genes showed similar patterns of expression between Groups A and B, but some groups were specific to either up or down regulation. One hundred and sixty genes were found to be differentially expressed between cumulus cells from oocytes that failed to fertilize on day 1 (Group A) and those from oocytes that reached the 8-cell stage on day 3 (Group B), in both replicate experiments. Of these 160 genes, 126 were characterized with relatively well defined biological functions. The breakdown of these 126 genes into functional categories is outlined in Table 1 (below) and FIG. 1. Genes involved in cell cycle, cell proliferation, apoptosis, oncogenesis, energy metabolism and mitochondrial proteins were expressed higher in group B than group A. Conversely, defense and ribosomal proteins are expressed higher in group A.

TABLE 1

Differential gene expression in cumulus cells

| Affymetrix ID | Accession | Gene/Protein Name | Fold Change |
|---|---|---|---|
| *Hormone and Hormone receptors* | | | |
| 218326_s_at | NM_018490 | G protein-coupled receptor 48 | 1.6 |
| 217816_s_at | NM_020357 | PEST-containing nuclear protein | 1.9 |
| 205258_at | NM_002193 | inhibin, beta B (activin AB beta polypeptide) | −1.5 |
| 210511_s_at | M13436 | inhibin, beta A (activin A, activin AB alpha polypeptide) | −1.9 |
| 201164_s_at | BG474429 | pumilio homolog 1 (*Drosophila*) | −1.5 |
| *Regulation of cell cycle and cell proliferation* | | | |
| 210212_x_at | BC002600 | mature T-cell proliferation 1 | 1.9 |
| 201202_at | NM_002592 | proliferating cell nuclear antigen | 1.8 |
| 202388_at | NM_002923 | regulator of G-protein signalling 2, 24 kDa | 1.7 |
| 201626_at | BG292233 | insulin induced gene 1 | 1.9 |
| 200043_at | NM_004450 | enhancer of rudimentary homolog (*Drosophila*) | 2.0 |
| 201218_at | NM_001329 | C-terminal binding protein 2 | 1.6 |
| 201938_at | NM_004642 | CDK2-associated protein 1 | 1.6 |
| 200711_s_at | NM_003197 | S-phase kinase-associated protein 1A (p19A) | 1.3 |
| 207974_s_at | NM_006930 | S-phase kinase-associated protein 1A (p19A) | 1.3 |
| 204093_at | NM_001239 | cyclin H | 1.4 |
| *Apoptosis* | | | |
| 213220_at | AV706096 | programmed cell death 4 (neoplastic transformation inhibitor) | 1.7 |
| 201758_at | NM_006292 | tumor susceptibility gene 101 | 1.7 |
| 205173_x_at | NM_001779 | CD58 antigen, (lymphocyte function-associated antigen 3) | 1.8 |
| 210907_s_at | BC002506 | programmed cell death 10 | 1.4 |
| 221478_at | AL132665 | BCL2/adenovirus E1B 19 kDa interacting protein 3-like | 1.3 |
| 217911_s_at | NM_004281 | BCL2-associated athanogene 3 | 1.3 |
| 201848_s_at | U15174 | BCL2/adenovirus E1B 19 kDa interacting protein 3 | 1.3 |
| 213047_x_at | AI278616 | SET translocation (myeloid leukemia-associated) | 1.5 |
| 209194_at | BC005334 | centrin, EF-hand protein, 2 | 1.5 |
| *Morphogenesis* | | | |
| 217858_s_at | NM_016607 | ALEX3 protein | 1.4 |
| 218729_at | NM_020169 | latexin protein | 1.4 |
| 203152_at | NM_003776 | mitochondrial ribosomal protein L40 | 1.7 |
| 212245_at | AL567779 | neural stem cell derived neuronal survival protein | 1.6 |
| 217731_s_at | NM_021999 | integral membrane protein 2B | 1.5 |
| 211758_x_at | BC005968 | ATP binding protein associated with cell differentiation | 1.5 |
| 203008_x_at | NM_005783 | ATP binding protein associated with cell differentiation | 1.4 |
| 201579_at | NM_005245 | FAT tumor suppressor homolog 1 (*Drosophila*) | 1.3 |
| 202544_at | NM_004124 | glia maturation factor, beta | 1.4 |
| 207922_s_at | NM_005882 | macrophage erythroblast attacher | −1.3 |
| 212094_at | AL582836 | paternally expressed 10 | 1.8 |
| 218330_s_at | NM_018162 | neuron navigator 2 | −1.6 |
| *Oncogenesis* | | | |
| 213423_x_at | AI884858 | Putative prostate cancer tumor suppressor | 1.5 |
| 209228_x_at | U42349 | Putative prostate cancer tumor suppressor | 1.4 |
| 214435_x_at | NM_005402 | v-ral simian leukemia viral oncogene homolog A (ras related) | 1.5 |
| 208841_s_at | AB014560 | Ras-GTPase activating protein SH3 domain-binding protein 2 | 1.3 |
| 200733_s_at | U48296 | protein tyrosine phosphatase type IVA, member 1 | 1.5 |
| *Defense response* | | | |
| 210514_x_at | AF226990 | HLA-G histocompatibility antigen, class I, G | −1.5 |
| 210208_x_at | BC003133 | HLA-B associated transcript 3 | −1.6 |
| 205067_at | NM_000576 | interleukin 1, beta | −2.1 |
| 39402_at | M15330 | interleukin 1, beta | −2.6 |
| 212895_s_at | AL527773 | active BCR-related gene | −1.4 |
| 213614_x_at | BE786672 | leukocyte receptor cluster (LRC) member 7 | −1.3 |
| *Structural* | | | |
| 201719_s_at | NM_001431 | erythrocyte membrane protein band 4.1-like 2 | 1.3 |
| 200836_s_at | NM_002375 | microtubule-associated protein 4 | −1.9 |
| 201949_x_at | AL572341 | capping protein (actin filament) muscle Z-line, beta | −1.3 |
| 204288_s_at | NM_021069 | Arg/Abl-interacting protein ArgBP2 | −1.7 |
| 32811_at | Cluster Incl. X98507 | myosin IC | −2.0 |
| 204805_s_at | NM_006026 | H1 histone family, member X | −1.3 |
| *Energy Metabolism* | | | |
| 208836_at | U51478 | ATPase, Na+/K+ transporting, beta 3 polypeptide | 1.5 |
| 209492_x_at | BC003679 | ATP synthase, H+ transporting, mitochondrial F0 complex, subunit e | 1.4 |

TABLE 1-continued

Differential gene expression in cumulus cells

| Affymetrix ID | Accession | Gene/Protein Name | Fold Change |
|---|---|---|---|
| 208899_x_at | gb | ATPase, H+ transporting, lysosomal 34 kDa, V1 subunit D | 1.4 |
| 221750_at | Consensus includes BG035985 | 3-hydroxy-3-methylglutaryl-Coenzyme A synthase 1 (soluble) | 1.5 |
| 202298_at | NM_004541 | NADH dehydrogenase (ubiquinone) 1 alpha subcomplex, 1, 7.5 kDa | 1.5 |
| 211023_at | AL117618 | pyruvate dehydrogenase (lipoamide) beta | 1.4 |
| 213564_x_at | Consensus includes BE042354 | lactate dehydrogenase B | 1.3 |
| 213129_s_at | Consensus includes AI970157 | glycine cleavage system protein H (aminomethyl carrier) | 1.4 |
| 201821_s_at | BC004439 | translocase of inner mitochondrial membrane 17 homolog A (yeast) | 1.4 |
| 215171_s_at | Consensus includes AK023063 | translocase of inner mitochondrial membrane 17 homolog A (yeast) | 1.3 |
| 218890_x_at | NM_016622 | mitochondrial ribosomal protein L35 | 7.4 |
| 217907_at | NM_014161 | mitochondrial ribosomal protein L18 | 1.3 |
| 209609_s_at | BC004517 | mitochondrial ribosomal protein L9 | 1.4 |
| | | Metabolism and Catabolism | |
| 210243_s_at | AF038661 | UDP-Gal: betaGlcNAc beta 1,4-galactosyltransferase, polypeptide 3 | −1.5 |
| 210950_s_at | BC003573 | farnesyl-diphosphate farnesyltransferase 1 | 1.3 |
| 32836_at | Cluster Incl. U56417 | 1-acylglycerol-3-phosphate O-acyltransferase 1 | −1.3 |
| 218487_at | BC000977 | aminolevulinate, delta-, dehydratase | 1.8 |
| 202854_at | NM_000194 | hypoxanthine phosphoribosyltransferase 1 (Lesch-Nyhan syndrome) | 1.5 |
| 210417_s_at | U81802 | phosphatidylinositol 4-kinase, catalytic, beta polypeptide | −1.7 |
| 204257_at | NM_021727 | fatty acid desaturase 3 | −1.4 |
| 216080_s_at | Consensus includes AC004770 | fatty acid desaturase 3 | −1.6 |
| 203946_s_at | U75667 | arginase, type II | 1.6 |
| 203743_s_at | NM_003211 | thymine-DNA glycosylase | 1.4 |
| 202208_s_at | BC001051 | ADP-ribosylation factor-like 7 | −2.4 |
| 218946_at | NM_015700 | HIRA interacting protein 5 | 1.5 |
| 201704_at | NM_001247 | ectonucleoside triphosphate diphosphohydrolase 6 (putative function) | −1.3 |
| | | Transporters | |
| 209109_s_at | U84895 | transmembrane 4 superfamily member 6 | 1.3 |
| 209681_at | AF153330 | solute carrier family 19 (thiamine transporter), member 2 | 1.5 |
| 209215_at | L11669 | tetracycline transporter-like protein | −1.3 |
| 204359_at | NM_013231 | fibronectin leucine rich transmembrane protein 2 | 1.3 |
| 200787_s_at | BC002426 | phosphoprotein enriched in astrocytes 15 | −1.5 |
| 209039_x_at | AF001434 | EH-domain containing 1 | −1.3 |
| 200612_s_at | NM_001282 | adaptor-related protein complex 2, beta 1 subunit | −1.5 |
| | | Signal Transduction | |
| 218618_s_at | NM_022763 | FAD104 | −2.0 |
| 202670_at | Consensus includes AI571419 | mitogen-activated protein kinase kinase 1 | 1.3 |
| 201811_x_at | NM_004844 | SH3-domain binding protein 5 (BTK-associated) | 1.5 |
| 38269_at | Cluster Incl. AL050147 | protein kinase D2 | −1.7 |
| | | Proteases | |
| 210024_s_at | AB017644 | ubiquitin-conjugating enzyme E2E 3 (UBC4/5 homolog, yeast) | 1.4 |
| 201471_s_at | NM_003900 | sequestosome 1 | −1.4 |
| 202376_at | NM_001085 | serine (or cysteine) proteinase inhibitor, clade A | −1.3 |
| 209017_s_at | U02389 | protease, serine, 15 | −1.3 |
| 200830_at | NM_002808 | proteasome (prosome, macropain) 26S subunit, non-ATPase, 2 | −1.4 |
| 212222_at | Consensus includes AU143855 | proteasome activator 200 kDa | 1.3 |
| | | Transcription control | |
| 218803_at | NM_018223 | checkpoint with forkhead and ring finger domains | −1.5 |
| 202142_at | BC003090 | COP9 homolog | 1.4 |
| 214281_s_at | Consensus includes AA524525 | zinc finger protein 363 | 1.6 |
| 200777_s_at | NM_014670 | basic leucine zipper and W2 domains 1 | 1.4 |
| 203787_at | NM_012446 | single-stranded DNA binding protein 2 | 1.7 |
| 201273_s_at | NM_003133 | signal recognition particle 9 kDa | 1.7 |

TABLE 1-continued

Differential gene expression in cumulus cells

| Affymetrix ID | Accession | Gene/Protein Name | Fold Change |
|---|---|---|---|
| 202678_at | NM_004492 | general transcription factor IIA, 2, 12 kDa | 1.3 |
| 201144_s_at | NM_004094 | eukaryotic translation initiation factor 2, subunit 1 alpha, 35 kDa | 1.5 |
| 201142_at | Consensus includes AA577698 | eukaryotic translation initiation factor 2, subunit 1 alpha, 35 kDa | 1.3 |
| 200647_x_at | NM_003752 | eukaryotic translation initiation factor 3, subunit 8, 110 kDa | −1.3 |
| | | Ribosomal Proteins | |
| 210646_x_at | BC001675 | ribosomal protein L13a | −1.3 |
| 200869_at | NM_000980 | ribosomal protein L18a | −1.4 |
| 202028_s_at | Consensus includes BC000603 | ribosomal protein L38 | −2.1 |
| | | Protein and RNA Processing | |
| 208713_at | Consensus includes BF724216 | E1B-55 kDa-associated protein 5 | 1.3 |
| 202209_at | NM_014463 | Lsm3 protein | 1.4 |
| 214113_s_at | Consensus includes AI738479 | RNA binding motif protein 8A | 1.6 |
| 200893_at | NM_004593 | splicing factor, arginine/serine-rich 10 (transformer 2 homolog, *Drosophila*) | 1.5 |
| 221515_s_at | BC001214 | leucine carboxyl methyltransferase | −1.3 |
| 203102_s_at | NM_002408 | mannosyl (alpha-1,6-)-glycoprotein beta-1,2-N-acetylglucosaminyltransferase | 1.5 |
| 204571_x_at | Consensus includes BE797213 | protein (peptidyl-prolyl cis/trans isomerase) NIMA-interacting, 4 (parvulin) | 1.4 |
| 214224_s_at | Consensus includes BE674061 | protein (peptidyl-prolyl cis/trans isomerase) NIMA-interacting, 4 (parvulin) | 1.4 |
| 202550_s_at | NM_004738 | VAMP (vesicle-associated membrane protein)-associated protein B and C | 1.4 |
| | | Other Functions | |
| 202946_s_at | NM_001155 | annexin A6 | −1.5 |
| 202377_at | NM_014962 | BTB (POZ) domain containing 3 | 1.5 |
| 203336_s_at | Consensus includes AW026535 | leptin receptor gene-related protein | 1.4 |
| 205753_at | Consensus includes AL548363 | integrin cytoplasmic domain-associated protein 1 | 1.5 |
| 206157_at | NM_002852 | pentaxin related gene, rapidly induced by IL (Pentraxin 3) | 1.7 |
| 221531_at | AF126181 | melanoma antigen, family D, 2 | −1.4 |
| 202228_s_at | AF309553 | recombination protein REC14 | 1.5 |
| 201381_x_at | NM_017455 | stromal cell derived factor receptor 1 | 1.3 |
| 217761_at | AF057356 | Siah-interacting protein | 1.3 |
| 217761_at | NM_018269 | SIPL protein | 1.4 |

Example 3

Pentraxin-3 Expression

Figure 2:
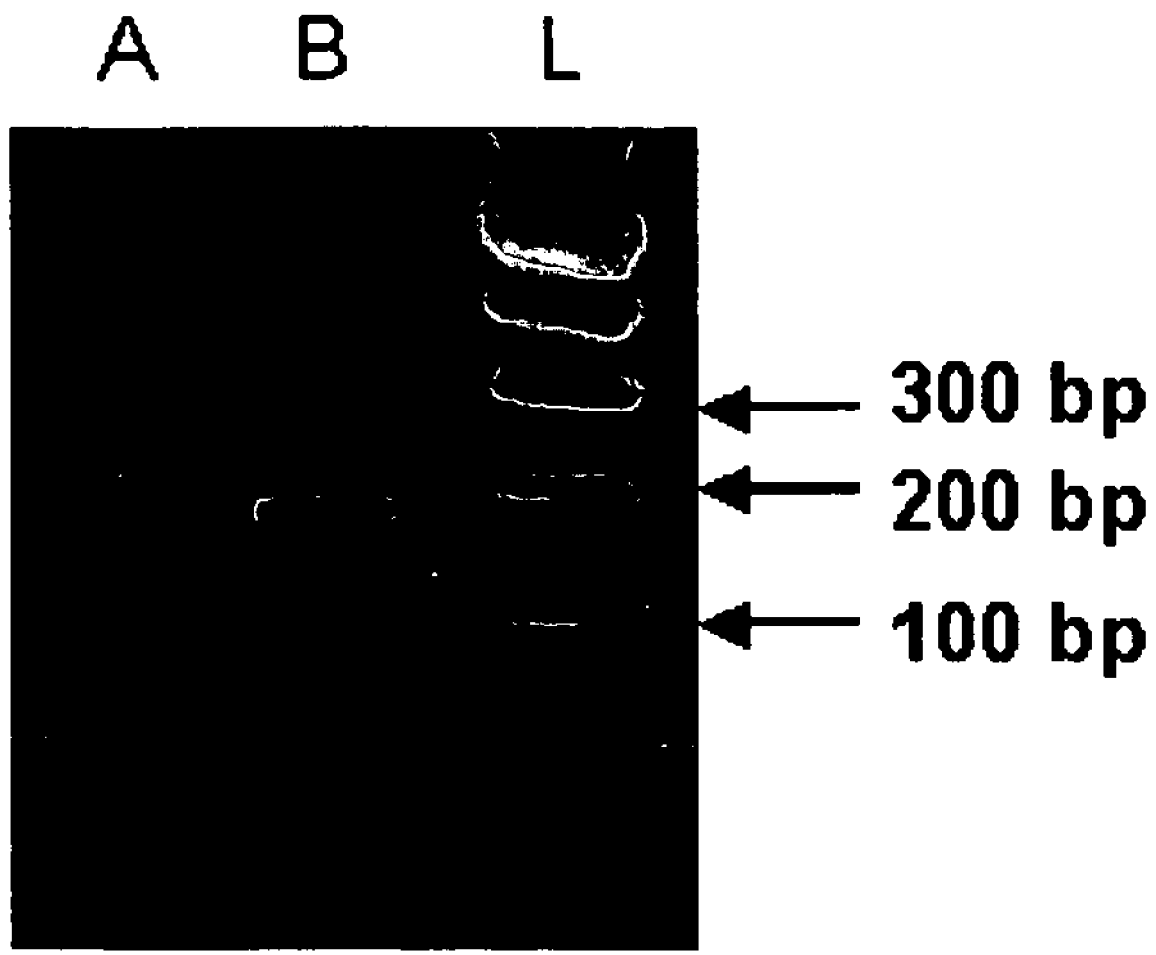
FIG. 2 shows the verification of the presence of Ptx3 mRNA in human cumulus cells by reverse-transcription and polymerase chain reaction.

Sixteen cumulus complexes from three patients (cause of infertility was unexplained for all three) were subjected to reverse-transcription PCR to confirm the presence of Ptx3 mRNA in human cumulus cells (See FIG. 2). The authenticity of the amplification product was verified by cloning and sequencing.

Figure 3:
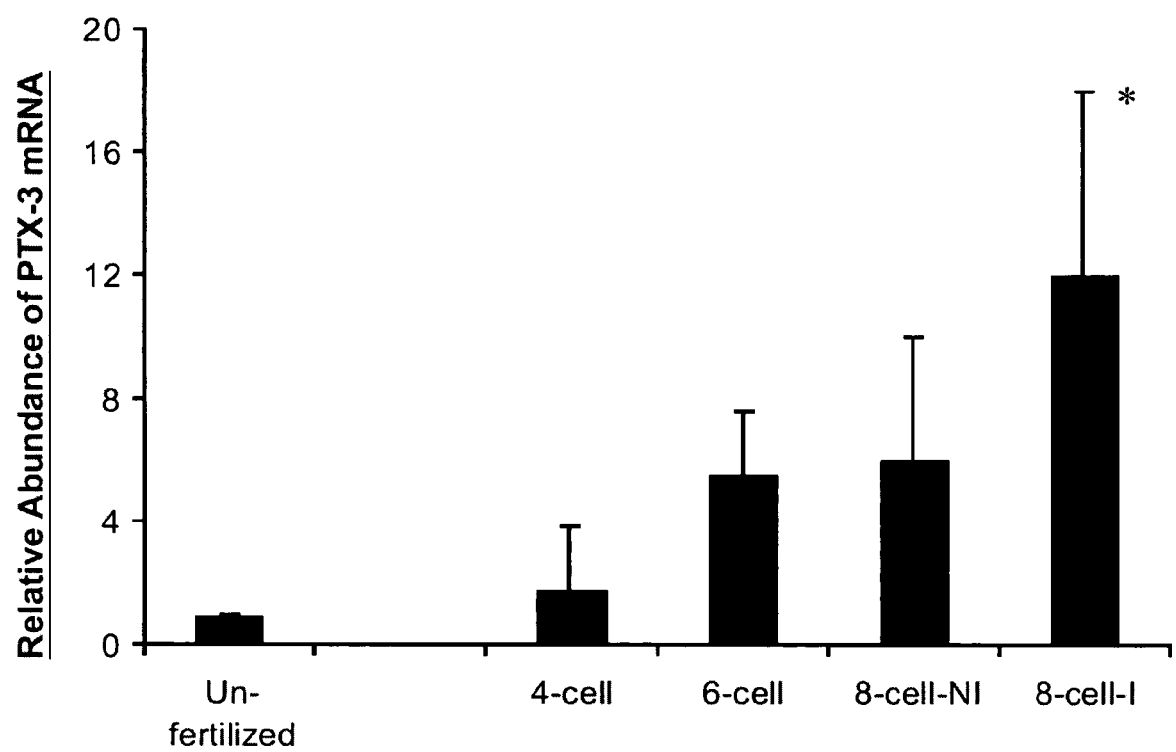
FIG. 3 shows the relative abundance of Ptx3 mRNA in human cumulus cells. "*" represents a significant difference compared to cumulus cells from unfertilized oocytes (p<0.01 using a t-test).

Real-time PCR was then employed to determine the relative abundance of Ptx3 mRNA in 98 cumulus complexes from 16 patients (See FIG. 3). The cause of infertility was tubal disease for two patients, endometriosis for two, polycystic ovarian syndrome for three and unexplained for the rest of the 16 patients. Compared with cumulus cells from unfertilized oocytes, cumulus cells from fertilized oocytes had 3- to 12-fold increases in the relative abundance of Ptx3 mRNA.

In order to further assess the correlation between Ptx3 expression in cumulus cells and the development potential (e.g., implantation potential) of the fertilized oocytes/embryos, fertilized oocytes/embryos that reached 8-cell stage on day 3 were divided into two groups: "8-cell-A" embryos were those that were transferred but did not establish a pregnancy, and "8-cell-B" embryos were those that were transferred and, at least some of them, implanted. The relative abundance of Ptx3 mRNA in cumulus cells from oocytes that resulted in "8-cell-B" embryos was 1.8 times greater than those from oocytes that resulted in "8-cell-A" embryos, and was 12 times greater ($p<0.01$) than those from oocytes that did not fertilize. Two embryo transfers involving the "8-cell-A" embryos also had one 6-cell embryo in each transfer, and one transfer of an "8-cell-B" embryo had also a 7-cell embryo with 30% of fragmentation.

All publications and patents mentioned in the above specification are herein incorporated by reference. Various modifications and variations of the described methods of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the present invention.

We claim:

1. A method of characterizing oocyte development potential of an oocyte comprising providing cumulus cells harvested from an oocyte cumulus complex comprising said oocyte and measuring the expression level of pentraxin 3 and a BCL 2 family member in said cumulus cells.

2. A method of determining the likelihood of an oocyte to become fertilized comprising:
   a) providing cumulus cells from an oocyte cumulus complex;
   b) measuring the level of expression of pentraxin 3 and a BCL 2 family member in said cumulus cells; and
   c) correlating said level of expression of said pentraxin 3 and said BCL 2 family member with the likelihood of said oocyte becoming fertilized.

3. A method of determining the likelihood of an oocyte implanting within the uterus of a female subject comprising:
   a) providing cumulus cells from an oocyte cumulus complex;
   b) measuring the level of expression of pentraxin 3 and a BCL 2 family member in said cumulus cells; and
   c) correlating said level of expression of said pentraxin 3 and said BCL 2 family member with the likelihood of said oocyte implanting within the uterus of a female subject.

* * * * *

UNITED STATES PATENT AND TRADEMARK OFFICE
CERTIFICATE OF CORRECTION

PATENT NO. : 7,572,601 B2
APPLICATION NO. : 11/251983
DATED : August 11, 2009
INVENTOR(S) : Xingqi Zhang et al.

Page 1 of 1

It is certified that error appears in the above-identified patent and that said Letters Patent is hereby corrected as shown below:

Column 1, second paragraph, to read as follows:

--This invention was funded, in part, under NIH grant U54 HD041857. The government has certain rights in the invention.--

Signed and Sealed this

Twentieth Day of October, 2009

David J. Kappos
*Director of the United States Patent and Trademark Office*